United States Patent
Lancaster et al.

(10) Patent No.: US 9,528,982 B2
(45) Date of Patent: Dec. 27, 2016

(54) BAD PHOSPHORYLATION DETERMINES OVARIAN CANCER CHEMO-SENSITIVITY AND PATIENT SURVIVAL

(71) Applicant: H. Lee Moffitt Cancer Center and Research Institute, Inc., Tampa, FL (US)

(72) Inventors: Johnathan Lancaster, Tampa, FL (US); Douglas Marchion, Seminole, FL (US); Dung-Tsa Chen, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/010,003

(22) Filed: Aug. 26, 2013

(65) Prior Publication Data

US 2014/0017703 A1    Jan. 16, 2014

Related U.S. Application Data

(63) Continuation of application No. PCT/US2012/026617, filed on Feb. 24, 2012.

(60) Provisional application No. 61/446,352, filed on Feb. 24, 2011.

(51) Int. Cl.
*G01N 33/574* (2006.01)
*G01N 33/50* (2006.01)

(52) U.S. Cl.
CPC .... *G01N 33/5044* (2013.01); *G01N 33/57449* (2013.01); *G01N 2440/14* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,599,912 B1 | 7/2003 | Au et al. | |
| 2007/0172844 A1 | 7/2007 | Lancaster et al. | |
| 2007/0254295 A1 | 11/2007 | Harvey et al. | |
| 2008/0108091 A1* | 5/2008 | Hennessy et al. | 435/7.23 |
| 2010/0233733 A1* | 9/2010 | Fantl | 435/7.23 |

OTHER PUBLICATIONS

Hugo Gene Nomenclature Committee, Symbol Report for BCL2L1, printed Oct. 2014.*
International Preliminary Report on Patentability for International Application No. PCT/US2012/026617, filing date of Feb. 24, 2012, issued on Aug. 27, 2013.
International Search Report for International Application No. PCT/US2012/026617, filing date of Feb. 24, 2012, issued on Sep. 27, 2012.
Marchion, D.C., et al., Bad Phosphorylation Determines Ovarian Cancer Chemosensitivity and Patient Survival. Clinical Cancer Research. Aug. 17, 2011, vol. 17, No. 19, pp. 6356-6366.
Chon, H.S. et al., The BCL2 antagonist of cell death influences endometrial cancer call sensitivity to cisplatin. Gynecologic Oncology. Oct. 26, 2011, vol. 124, No. 1, pp. 119-124.
Baker, Salvage therapy for recurrent epithelial ovarian cancer. Hematol Oncol Clin North Am 2003;17:977-988.
Benedetti, et al., Modulation of survival pathways in ovarian carcinoma cell lines resistant to platinum compounds. Mol Cancer Ther 2008;7:679-687.
Bild, et al., Oncogenic pathway signatures in human cancers as a guide to targeted therapies. Nature 2006;439:353-357.
Bolstad, et al., A comparison of normalization methods for high density oligonucleotide array data based on variance and bias. Bioinformatics 2003;19:185-193.
Boren, et al., MicroRNAs and their target messenger RNAs associated with ovarian cancer response to chemotherapy. Gynecol Oncol 2009;113:249-255.
Carroll, et al., Genome-wide analysis of estrogen receptor binding sites. Nat Genet 2006;38:1289-97.
Chanrion, et al., A gene expression signature that can predict the recurrence of tamoxifen-treated primary breast cancer. Clin Cancer Res 2008;14:1744-1752.
Chen, et al., Trophic factor induction of human umbilical cord blood cells in vitro and in vivo. J Neural Eng 2007;4:130-145.
Chen, et al., Proliferative genes dominate malignancy-risk gene signature in histologically normal breast tissue. Breast Cancer Res Treat 2010;119:335-46.
Chon, et al., The BCL2 antagonist of cell death pathway influences endometrial cancer cell sensitivity to cisplatin, Gynecology Oncology, 124 (2012) pp. 119-124.
Danial and Korsmeyer, Cell death: critical control points. Cell 2004;116:205-219.
Dejean, et al., Oligomeric Bax is a component of the putative cytochrome c release channel MAC, mitochondrial apoptosis-induced channel. Mol Biol Cell 2005;16:2424-2432.

(Continued)

*Primary Examiner* — Laura B Goddard
(74) *Attorney, Agent, or Firm* — Michele L. Lawson; Robert J. Varkonyi; Smith & Hopen, P.A.

(57) ABSTRACT

Despite initial sensitivity BAD-protein phosphorylation were evaluated in patient samples and cell lines as determinants of chemo-sensitivity and/or clinical outcome, and as therapeutic targets. Induced in-vitro OVCA cisplatin-resistance was associated with BAD-pathway expression. Expression of the pathway was also associated with resistance of 7 different cancers cell-types to 8 chemotherapeutic agents. Phosphorylation of the BAD-protein was associated with platinum-resistance in OVCA cells and primary OVCA specimens, and also overall patient survival. Targeted modulation of BAD-phosphorylation levels influenced cisplatin-sensitivity. A 47-gene BAD-pathway signature was associated in-vitro phospho-BAD levels and with survival of 838 patients with ovarian, breast, colon, and brain cancer. The survival advantage associated with both BAD-phosphorylation and also the BAD-pathway signature was independent of surgical cytoreductive status. The BAD apoptosis pathway influences human cancer chemo-sensitivity and overall survival. The pathway is useful as a biomarker of therapeutic response, patient survival, and therapeutic target.

15 Claims, 33 Drawing Sheets

(56) References Cited

OTHER PUBLICATIONS del Peso, et al., Interleukin-3-induced phosphorylation of BAD through the protein kinase Akt. Science 1997;278:687-689.
Desagher, et al., Bid-induced conformational change of Bax is responsible for mitochondrial cytochrome c release during apoptosis. J Cell Biol 1999;144:891-901.
Dressman, et al., An integrated genomic-based approach to individualized treatment of patients with advanced-stage ovarian cancer. J Clin Oncol 2007;25:517-525.
Efron and Tibshirani, Empirical bayes methods and false discovery rates for microarrays. Genet Epidemiol 2002; 23:70-86.
Godwin, et al., High resistance to cisplatin in human ovarian cancer cell lines is associated with marked increase of glutathione synthesis. Proc Natl Acad Sci U S A 1992;89:3070-3074.
Hansen, et al., New cytostatic drugs in ovarian cancer. Ann Oncol 1993;4 Suppl 4:63-70.
Herrin and Thigpen, Chemotherapy for ovarian cancer: current concepts. Semin Surg Oncol 1999;17:181-188.
Irizarry, et al., Exploration, normalization, and summaries of high density oligonucleotide array probe level data. Biostatistics 2003;4:249-264.
Jazaeri, et al., Gene expression profiles associated with response to chemotherapy in epithelial ovarian cancers. Clin Cancer Res 2005;11:6300-6310.
Johnson, et al., Relationship between platinum-DNA adduct formation and removal and cisplatin cytotoxicity in cisplatin-sensitive and -resistant human ovarian cancer cells. Cancer Res 1994;54:5911-5916.
Johnson, et al., Increased platinum-DNA damage tolerance is associated with cisplatin resistance and cross-resistance to various chemotherapeutic agents in unrelated human ovarian cancer cell lines. Cancer Res 1997;57:850-856.
Klumpp, et al., Protein phosphatase type 2C dephosphorylates BAD. Neurochem Int 2003;42:555-560.
Kuwana, et al., Bid, Bax, and lipids cooperate to form supramolecular openings in the outer mitochondrial membrane. Cell 2002;111:331-342.
Lee, et al., Gene expression analysis of glioblastomas identifies the major molecular basis for the prognostic benefit of younger age. BMC Med Genomics 2008;1:52.
Lizcano, et al., Regulation of BAD by cAMP-dependent protein kinase is mediated via phosphorylation of a novel site, Ser155. Biochem J 2000;349:547-557.
Ma, et al., Gene expression profiles of human breast cancer progression. Proc Natl Acad Sci USA 2003;100:5974-79.
Mabuchi, et al., Inhibition of Phosphorylation of BAD and Raf-1 by Akt Sensitizes Human Ovarian Cancer Cells to Paclitaxel, vol. 277, No. 36, Issue of Sep. 6, 2002, The Journal of Biological Chemistry, pp. 33490-33500.
Marchion, et al., Synergistic interaction between histone deacetylase and topoisomerase II inhibitors is mediated through topoisomerase IIbeta. Clin Cancer Res 2005;11:8467-8475.
Marchion, et al., BAD Phosphorylation Determines Ovarian Cancer Chemosensitivity and Patient Survival, Clinical Cancer Research, 17 (19) Oct. 1, 2011.
Miller, et al., Reporting results of cancer treatment. Cancer 1981;47:207-14.
Nutt, et al., Gene expression-based classification of malignant gliomas correlates better with survival than histological classification. Cancer Res 2003;63:1602-1607.
Hayakawa, et al., Inhibition of BAD Phosphorylation Either at Serine 112 via Extracellular signal-regulated protein kinase Cascade or at Serine 136 via Akt Cascade Sensitizes Human Ovarian Cancer Cells to Cisplatin, Cancer Research, 60, Nov. 1, 2000, pp. 5988-5994.
Raponi, et al., Gene expression signatures for predicting prognosis of squamous cell and adenocarcinomas of the lung. Cancer Res. Aug. 1, 2006;66(15):7466-72.
Rustin, et al., Defining response of ovarian carcinoma to initial chemotherapy according to serum CA 125. J Clin Oncol 1996;14:1545-51.
Rustin, et al., Use of tumour markers in monitoring the course of ovarian cancer. Ann Oncol 1999;10 Suppl 1:21-7.
Smith. Et al., (2010) Experimentally derived metastasis gene expression profile predicts recurrence and death in patients with colon cancer. Gastroenterology 138: 958-968.
Tan, et al., BAD Ser-155 phosphorylation regulates BAD/Bcl-XL interaction and cell survival. J Biol Chem 2000; 275:25865-25869.
Tothill, et al. Novel molecular subtypes of serous and endometrioid ovarian cancer linked to clinical outcome. Clin Cancer Res. 2008;14:5198-208.
Tusher, et al., Significance analysis of microarrays applied to the ionizing radiation response. Proc Natl Acad Sci U S A 2001;98:5116-5121.
Wang, et al., Gene-expression profiles to predict distant metastasis of lymph-node-negative primary breast cancer. Lancet 2005;365:671-679.
Yang, et al., Bad, a heterodimeric partner for Bcl-XL and Bcl-2, displaces Bax and promotes cell death. Cell 1995;80:285-291.
Yang, et al., Calcineurin-mediated BAD Ser155 dephosphorylation in ammonia-induced apoptosis of cultured rat hippocampal neurons. Neurosci Lett 2004;357:73-75.
Zhou, et al., Growth factors inactivate the cell death promoter BAD by phosphorylation of its BH3 domain on Ser155. J Biol Chem 2000;275:25046-25051.
Tsai, Hsieh-Chin et al. Cyclic AMP-dependent protein kinase A negatively regulates conidia formation by the tangerine pathotype of Alternaria alternata. World J Microbiol Biotechnol (2013) 29:289-300.

\* cited by examiner

| Probeset | p value | Probe Set ID | Gene Symbol | Gene Title |
|---|---|---|---|---|
| 209682_at | 7.26E-06 | 209682_at | CBLB | Cas-Br-M (murine) ecotropic retroviral transforming sequence b |
| 201421_s_at | 2.96E-05 | 201421_s_at | WDR77 | WD repeat domain 77 |
| 203291_at | 3.28E-05 | 203291_at | CNOT4 | CCR4-NOT transcription complex, subunit 4 |
| 202208_s_at | 4.78E-05 | 202208_s_at | ARL4C | ADP-ribosylation factor-like 4C |
| 202600_s_at | 4.91E-05 | 202600_s_at | NRIP1 | nuclear receptor interacting protein 1 |
| 209205_s_at | 5.23E-05 | 209205_s_at | LMO4 | LIM domain only 4 |
| 214793_at | 7.29E-05 | 214793_at | DUSP7 | dual specificity phosphatase 7 |
| 210212_x_at | 0.00015073 | 210212_x_at | MTCP1NB | mature T-cell proliferation 1 neighbor |
| 207871_s_at | 0.00016611 | 207871_s_at | ST7 | suppression of tumorigenicity 7 |
| 219100_at | 0.00018351 | 219100_at | OBFC1 | oligonucleotide/oligosaccharide-binding fold containing 1 |
| 201929_s_at | 0.00021016 | 201929_s_at | PKP4 | plakophilin 4 |
| 212013_at | 0.0002114 | 212013_at | PXDN | peroxidasin homolog (Drosophila) |
| 203905_at | 0.00022733 | 203905_at | PARN | poly(A)-specific ribonuclease (deadenylation nuclease) |
| 200759_x_at | 0.00023647 | 200759_x_at | NFE2L1 | nuclear factor (erythroid-derived 2)-like 1 |
| 207128_s_at | 0.0002696 | 207128_s_at | ZNF223 | zinc finger protein 223 |
| 201498_at | 0.0002922 | 201498_at | USP7 | ubiquitin specific peptidase 7 (herpes virus-associated) |
| 211031_s_at | 0.00029462 | 211031_s_at | CLIP2 | CAP-GLY domain containing linker protein 2 |
| 203164_at | 0.00029797 | 203164_at | SLC33A1 | solute carrier family 33 (acetyl-CoA transporter), member 1 |
| 219077_s_at | 0.00030611 | 219077_s_at | WWOX | WW domain containing oxidoreductase |
| 201420_s_at | 0.00030762 | 201420_s_at | WDR77 | WD repeat domain 77 |
| 201474_s_at | 0.00032774 | 201474_s_at | ITGA3 | integrin, alpha 3 (antigen CD49C, alpha 3 subunit of VLA-3 receptor) |
| 201484_at | 0.00033507 | 201484_at | SUPT4H1 | suppressor of Ty 4 homolog 1 (S. cerevisiae) |
| 201158_at | 0.00034733 | 201158_at | NMT1 | N-myristoyltransferase 1 |
| 202214_s_at | 0.00039681 | 202214_s_at | CUL4B | cullin 4B |
| 210826_x_at | 0.00045808 | 210826_x_at | RAD17 | RAD17 homolog (S. pombe) |
| 218951_s_at | 0.00052783 | 218951_s_at | PLCXD1 | phosphatidylinositol-specific phospholipase C, X domain containing 1 |
| 222244_s_at | 0.00053528 | 222244_s_at | TUG1 | taurine upregulated 1 (non-protein coding) |
| 207163_s_at | 0.00054276 | 207163_s_at | AKT1 | v-akt murine thymoma viral oncogene homolog 1 |
| 218307_at | 0.00054477 | 218307_at | RSAD1 | radical S-adenosyl methionine domain containing 1 |
| 203016_s_at | 0.00070435 | 203016_s_at | SSX2IP 12/34. | synovial sarcoma, X breakpoint 2 interacting protein |
| 210861_s_at | 0.00073179 | 210861_s_at | WISP3 | WNT1 inducible signaling pathway protein 3 |
| 218095_s_at | 0.00078461 | 218095_s_at | TMEM165 | transmembrane protein 165 |

Figure 12 continued

| Probe ID | p-value | Gene ID | Gene Symbol | Description |
|---|---|---|---|---|
| 201778_s_at | 0.00084222 | 201778_s_at | KIAA0494 | KIAA0494 |
| 209931_s_at | 0.00089085 | 209931_s_at | FKBP1B /// M | FK506 binding protein 1B, 12.6 kDa /// major facilitator superfamily domain-containing protein 2b |
| 200758_s_at | 0.00091056 | 200758_s_at | NFE2L1 | nuclear factor (erythroid-derived 2)-like 1 |
| 219206_x_at | 0.00096111 | 219206_x_at | TMBIM4 | transmembrane BAX inhibitor motif containing 4 |
| 221874_at | 0.00098486 | 221874_at | KIAA1324 | KIAA1324 |
| 201353_s_at | 0.00100233 | 201353_s_at | BAZ2A | bromodomain adjacent to zinc finger domain, 2A |
| 212435_at | 0.0010082 | 212435_at | TRIM33 | tripartite motif-containing 33 |
| 217921_at | 0.0010093 | 217921_at | MAN1A2 | mannosidase, alpha, class 1A, member 2 |
| 213229_at | 0.00101387 | 213229_at | DICER1 | dicer 1, ribonuclease type III |
| 205340_at | 0.00101513 | 205340_at | ZBTB24 | zinc finger and BTB domain containing 24 |
| 218665_at | 0.00101615 | 218665_at | FZD4 | frizzled homolog 4 (Drosophila) |
| 207270_x_at | 0.00102491 | 207270_x_at | CD300C | CD300c molecule |
| 203679_at | 0.00102514 | 203679_at | TMED1 | transmembrane emp24 protein transport domain containing 1 |
| 205512_s_at | 0.00108723 | 205512_s_at | AIFM1 | apoptosis-inducing factor, mitochondrion-associated, 1 |
| 201776_s_at | 0.00110892 | 201776_s_at | KIAA0494 | KIAA0494 |
| 213325_at | 0.00113717 | 213325_at | PVRL3 | poliovirus receptor-related 3 |
| 216862_s_at | 0.00120157 | 216862_s_at | MTCP1NB | mature T-cell proliferation 1 neighbor |
| 221819_at | 0.00122436 | 221819_at | RAB35 | RAB35, member RAS oncogene family |
| 212436_at | 0.00123183 | 212436_at | TRIM33 | tripartite motif-containing 33 |
| 218103_at | 0.00132475 | 218103_at | FTSJ3 | FtsJ homolog 3 (E. coli) |
| 200659_s_at | 0.00133889 | 200659_s_at | PHB | prohibitin |
| 220208_at | 0.00133933 | 220208_at | ADAMTS13 | ADAM metallopeptidase with thrombospondin type 1 motif, 13 |
| 202511_s_at | 0.00134588 | 202511_s_at | ATG5 | ATG5 autophagy related 5 homolog (S. cerevisiae) |
| 205013_s_at | 0.00139343 | 205013_s_at | ADORA2A /// | adenosine A2a receptor /// cytospin A |
| 212337_at | 0.00141404 | 212337_at | TUG1 | taurine upregulated 1 (non-protein coding) |
| 202207_at | 0.00145064 | 202207_at | ARL4C | ADP-ribosylation factor-like 4C |
| 202522_at | 0.00147388 | 202522_at | PITPNB | phosphatidylinositol transfer protein, beta |
| 202290_at | 0.00149004 | 202290_at | PDAP1 | PDGFA associated protein 1 |
| 222114_x_at | 0.00149104 | 222114_x_at | WDR55 13/34 | WD repeat domain 55 |
| 200861_at | 0.00155092 | 200861_at | CNOT1 | CCR4-NOT transcription complex, subunit 1 |
| 204136_at | 0.00158439 | 204136_at | COL7A1 | collagen, type VII, alpha 1 |
| 204622_x_at | 0.00162295 | 204622_x_at | NR4A2 | nuclear receptor subfamily 4, group A, member 2 |
| 202512_s_at | 0.00164019 | 202512_s_at | ATG5 | ATG5 autophagy related 5 homolog (S. cerevisiae) |

Figure 12 continued

| Probe ID | p-value | Gene Symbol | Description |
|---|---|---|---|
| 200969_at | 0.00166691 | SERP1 | stress-associated endoplasmic reticulum protein 1 |
| 220191_at | 0.00170077 | GKN1 | gastrokine 1 |
| 220212_s_at | 0.00176531 | THADA | thyroid adenoma associated |
| 218740_s_at | 0.00185041 | CDK5RAP3 | CDK5 regulatory subunit associated protein 3 |
| 204928_s_at | 0.00185377 | SLC10A3 | solute carrier family 10 (sodium/bile acid cotransporter family), member 3 |
| 202850_at | 0.0018788 | ABCD3 | ATP-binding cassette, sub-family D (ALD), member 3 |
| 209294_x_at | 0.00188457 | TNFRSF10B | tumor necrosis factor receptor superfamily, member 10b |
| 208093_s_at | 0.00191492 | NDEL1 | nudE nuclear distribution gene E homolog (A. nidulans)-like 1 |
| 206877_at | 0.00198677 | MXD1 | MAX dimerization protein 1 |
| 221031_s_at | 0.0020102 | APOLD1 | apolipoprotein L domain containing 1 |
| 221196_x_at | 0.00207922 | BRCC3 | BRCA1/BRCA2-containing complex, subunit 3 |
| 202776_at | 0.0020801 | DNTTIP2 | deoxynucleotidyltransferase, terminal, interacting protein 2 |
| 207656_s_at | 0.00209884 | ACOX1 | acyl-Coenzyme A oxidase 1, palmitoyl |
| 201944_at | 0.00210789 | HEXB | hexosaminidase B (beta polypeptide) |
| 207701_at | 0.00213795 | C22orf24 | chromosome 22 open reading frame 24 |
| 222256_s_at | 0.00214398 | JMJD7 /// JMJD7-PLA2G4B | JM jumonji domain containing 7 /// JMJD7-PLA2G4B readthrough transcript |
| 206572_x_at | 0.00216894 | ZNF85 | zinc finger protein 85 |
| 200670_at | 0.00228585 | XBP1 | X-box binding protein 1 |
| 202484_s_at | 0.0023178 | MBD2 | methyl-CpG binding domain protein 2 |
| 210876_at | 0.00237203 | ANXA2P1 | annexin A2 pseudogene 1 |
| 208383_s_at | 0.00242953 | PCK1 | phosphoenolpyruvate carboxykinase 1 (soluble) |
| 210407_at | 0.00245933 | PPM1A | protein phosphatase 1A (formerly 2C), magnesium-dependent, alpha isoform |
| 217312_s_at | 0.00253221 | COL7A1 | collagen, type VII, alpha 1 |
| 212645_x_at | 0.00257842 | BRE | brain and reproductive organ-expressed (TNFRSF1A modulator) |
| 202939_at | 0.00260985 | ZMPSTE24 | zinc metallopeptidase (STE24 homolog, S. cerevisiae) |
| 201455_s_at | 0.00261042 | NPEPPS | aminopeptidase puromycin sensitive |
| 212564_at | 0.00263664 | KCTD2 14/34 | potassium channel tetramerisation domain containing 2 |
| 215804_at | 0.00264696 | EPHA1 | EPH receptor A1 |
| 201004_at | 0.00267522 | SSR4 | signal sequence receptor, delta (translocon-associated protein delta) |
| 214036_at | 0.00268232 | EFNA5 | ephrin-A5 |
| 202607_at | 0.0027185 | NDST1 | N-deacetylase/N-sulfotransferase (heparan glucosaminyl) 1 |

Figure 12 continued

| Probe ID | Value | Gene | Description |
|---|---|---|---|
| 220488_s_at | 0.0027893 | BCAS3 | breast carcinoma amplified sequence 3 |
| 214678_x_at | 0.002281902 | ZFX | zinc finger protein, X-linked |
| 212057_at | 0.00283424 | KIAA0182 | KIAA0182 |
| 210054_at | 0.0028809 | HAUS3 | HAUS augmin-like complex, subunit 3 |
| 209435_s_at | 0.00228877 | ARHGEF2 | Rho/Rac guanine nucleotide exchange factor (GEF) 2 |
| 205926_at | 0.00294989 | IL27RA | interleukin 27 receptor, alpha |
| 222031_at | 0.0029549 | LOC286434 | hypothetical protein LOC286434 /// similar to Serine/threonine-protein kinase PRKX (Protein kinase PKX1) /// similar to hCG1981372 |
| 209833_at | 0.00298393 | CRADD | CASP2 and RIPK1 domain containing adaptor with death domain |
| 216264_s_at | 0.00298479 | LAMB2 | laminin, beta 2 (laminin S) |
| 214237_x_at | 0.00298573 | PAWR | PRKC, apoptosis, WT1, regulator |
| 215470_at | 0.00303554 | GTF2H2B | general transcription factor IIH, polypeptide 2B |
| 206103_at | 0.00305992 | RAC3 | ras-related C3 botulinum toxin substrate 3 (rho family, small GTP binding protein Rac3) |
| 209407_s_at | 0.003087 | DEAF1 | deformed epidermal autoregulatory factor 1 (Drosophila) |
| 205968_at | 0.00310499 | KCNS3 | potassium voltage-gated channel, delayed-rectifier, subfamily S, member 3 |
| 201829_at | 0.00311746 | NET1 | neuroepithelial cell transforming 1 |
| 213942_at | 0.00315485 | MEGF6 | multiple EGF-like-domains 6 |
| 202206_at | 0.00317669 | ARL4C | ADP-ribosylation factor-like 4C |
| 202710_at | 0.00318349 | BET1 | blocked early in transport 1 homolog (S. cerevisiae) |
| 221656_s_at | 0.00321634 | ARHGEF10L | Rho guanine nucleotide exchange factor (GEF) 10-like |
| 211228_s_at | 0.00322764 | RAD17 | RAD17 homolog (S. pombe) |
| 209440_at | 0.00325446 | PRPS1 | phosphoribosyl pyrophosphate synthetase 1 |
| 212291_at | 0.00332898 | HIPK1 | homeodomain interacting protein kinase 1 |
| 209996_x_at | 0.00334583 | PCM1 | pericentriolar material 1 |
| 221190_s_at | 0.00334774 | C18orf8 | chromosome 18 open reading frame 8 |
| 202590_s_at | 0.00339804 | PDK2 | pyruvate dehydrogenase kinase, isozyme 2 |
| | | 15/34 | |
| 208374_s_at | 0.00334369 | CAPZA1 | capping protein (actin filament) muscle Z-line, alpha 1 |
| 207983_s_at | 0.00346516 | STAG2 | stromal antigen 2 |
| 221455_s_at | 0.00348208 | WNT3 | wingless-type MMTV integration site family, member 3 |
| 200821_at | 0.00349265 | LAMP2 | lysosomal-associated membrane protein 2 |
| 221788_at | 0.00355711 | --- | --- |
| 214257_s_at | 0.00357767 | --- | --- |

Figure 12 continued

| Probe ID | Value | Gene | Description |
|---|---|---|---|
| 208816_x_at | 0.0035868 | 208816_x_at ANXA2P2 | annexin A2 pseudogene 2 |
| 218277_s_at | 0.0036550 | 218277_s_at DHX40 | DEAH (Asp-Glu-Ala-His) box polypeptide 40 |
| 218738_s_at | 0.0036722 | 218738_s_at RNF138 | ring finger protein 138 |
| 205963_s_at | 0.0036746 | 205963_s_at DNAJA3 | DnaJ (Hsp40) homolog, subfamily A, member 3 |
| 213090_s_at | 0.0036835 | 213090_s_at TAF4 | TAF4 RNA polymerase II, TATA box binding protein (TBP)-associated factor, 135kDa |
| 37802_r_at | 0.0037453 | 37802_r_at FAM63B | family with sequence similarity 63, member B |
| 220583_at | 0.0037713 | 220583_at --- | --- |
| 209845_at | 0.0037869 | 209845_at MKRN1 | makorin ring finger protein 1 |
| 211733_x_at | 0.0038067 | 211733_x_at SCP2 | sterol carrier protein 2 |
| 206698_at | 0.0038465 | 206698_at XK | X-linked Kx blood group (McLeod syndrome) |
| 216906_at | 0.0038624 | 216906_at ST14 | suppression of tumorigenicity 14 (colon carcinoma) |
| 212717_at | 0.0038850 | 212717_at PLEKHM1 | pleckstrin homology domain containing, family M (with RUN domain) member 1 |
| 202506_at | 0.0039400 | 202506_at SSFA2 | sperm specific antigen 2 |
| 209597_s_at | 0.0039693 | 209597_s_at PNMA2 | paraneoplastic antigen MA2 |
| 212156_at | 0.0039713 | 212156_at VPS39 | vacuolar protein sorting 39 homolog (S. cerevisiae) |
| 206518_s_at | 0.0039805 | 206518_s_at RGS9 | regulator of G-protein signaling 9 |
| 212497_at | 0.0040033 | 212497_at MAPK1IP1L | mitogen-activated protein kinase 1 interacting protein 1-like |
| 209022_at | 0.0040147 | 209022_at STAG2 | stromal antigen 2 |
| 203464_s_at | 0.0040426 | 203464_s_at EPN2 | epsin 2 |
| 214352_s_at | 0.0041167 | 214352_s_at KRAS | v-Ki-ras2 Kirsten rat sarcoma viral oncogene homolog |
| 219401_at | 0.0041318 | 219401_at XYLT2 | xylosyltransferase II |
| 203921_at | 0.0041697 | 203921_at CHST2 | carbohydrate (N-acetylglucosamine-6-O) sulfotransferase 2 |
| 209605_at | 0.0041704 | 209605_at TST | thiosulfate sulfurtransferase (rhodanese) |
| 217138_x_at | 0.0041974 | 217138_x_at IGL@ | Immunoglobulin lambda locus |
| 205070_at | 0.0042010 | 205070_at ING3 | inhibitor of growth family, member 3 |
| 203783_x_at | 0.0042342 | 203783_x_at POLRMT 16/34 | polymerase (RNA) mitochondrial (DNA directed) |
| 218688_at | 0.0042359 | 218688_at DAK | dihydroxyacetone kinase 2 homolog (S. cerevisiae) |
| 202855_s_at | 0.0042444 | 202855_s_at SLC16A3 | solute carrier family 16, member 3 (monocarboxylic acid transporter 4) |
| 203353_s_at | 0.0042922 | 203353_s_at MBD1 | methyl-CpG binding domain protein 1 |
| 222113_s_at | 0.0043561 | 222113_s_at EPS15L1 | epidermal growth factor receptor pathway substrate 15-like 1 |

Figure 12 continued

| | | | |
|---|---|---|---|
| 212064_x_at | 0.00435661 212064_x_at | MAZ | MYC-associated zinc finger protein (purine-binding transcription factor) |
| 209015_s_at | 0.00437532 209015_s_at | DNAJB6 | DnaJ (Hsp40) homolog, subfamily B, member 6 |
| 207193_at | 0.00439676 207193_at | AGRP | agouti related protein homolog (mouse) |
| 213628_at | 0.0044049 213628_at | CLCC1 | chloride channel CLIC-like 1 |
| 217608_at | 0.00444133 217608_at | SFRS12IP1 | SFRS12-interacting protein 1 |
| 208163_s_at | 0.00444137 208163_s_at | OSBPL7 | oxysterol binding protein-like 7 |
| 210421_s_at | 0.00444885 210421_s_at | SLC24A1 | solute carrier family 24 (sodium/potassium/calcium exchanger), member 1 |
| 213308_at | 0.00446894 213308_at | SHANK2 | SH3 and multiple ankyrin repeat domains 2 |
| 52169_at | 0.0045045 52169_at | STRADA | STE20-related kinase adaptor alpha |
| 210546_x_at | 0.00450493 210546_x_at | CTAG1A | cancer/testis antigen 1A /// cancer/testis antigen 1B |
| 219246_s_at | 0.00450499 219246_s_at | OGFOD2 | 2-oxoglutarate and iron-dependent oxygenase domain containing 2 |
| 215093_at | 0.00450516 215093_at | NSDHL | NAD(P) dependent steroid dehydrogenase-like |
| 207688_s_at | 0.0045168 207688_s_at | --- | --- |
| 217321_x_at | 0.00452753 217321_x_at | ATXN3 | Ataxin 3 |
| 218763_at | 0.00455935 218763_at | STX18 | syntaxin 18 |
| 222239_s_at | 0.00456062 222239_s_at | INTS6 | integrator complex subunit 6 |
| 214865_at | 0.00458243 214865_at | DOT1L | DOT1-like, histone H3 methyltransferase (S. cerevisiae) |
| 213545_x_at | 0.00458918 213545_x_at | SNX3 | sorting nexin 3 |
| 200971_s_at | 0.00459251 200971_s_at | SERP1 | stress-associated endoplasmic reticulum protein 1 |
| 221194_s_at | 0.00460666 221194_s_at | RNFT1 | ring finger protein, transmembrane 1 |
| 219516_at | 0.00462892 219516_at | TRPV4 | transient receptor potential cation channel, subfamily V, member 4 |
| 53912_at | 0.00476382 53912_at | SNX11 | sorting nexin 11 |
| 203857_s_at | 0.00484265 203857_s_at | PDIA5 | protein disulfide isomerase family A, member 5 |
| 206127_at | 0.00485053 206127_at | ELK3 | ELK3, ETS-domain protein (SRF accessory protein 2) |
| 220762_s_at | 0.00487304 220762_s_at | GNB1L | guanine nucleotide binding protein (G protein), beta polypeptide 1-like |
| 219861_at | 0.0048797 219861_at | DNAJC17 17/34 | DnaJ (Hsp40) homolog, subfamily C, member 17 |
| 217653_x_at | 0.00490443 217653_x_at | --- | --- |
| 201850_at | 0.00493902 201850_at | CAPG | capping protein (actin filament), gelsolin-like |
| 210405_x_at | 0.00494743 210405_x_at | TNFRSF10B | tumor necrosis factor receptor superfamily, member 10b |
| 203017_s_at | 0.00495832 203017_s_at | SSX2IP | synovial sarcoma, X breakpoint 2 interacting protein |
| 211661_x_at | 0.00503415 211661_x_at | PTAFR | platelet-activating factor receptor |

Figure 12 continued

| | | | |
|---|---|---|---|
| 220646_s_at | 0.00506836 | 220646_s_at KLRF1 | killer cell lectin-like receptor subfamily F, member 1 |
| 212026_s_at | 0.00509003 | 212026_s_at EXOC7 | exocyst complex component 7 |
| 218712_at | 0.00512787 | 218712_at C1orf109 | chromosome 1 open reading frame 109 |
| 203196_at | 0.00512873 | 203196_at ABCC4 | ATP-binding cassette, sub-family C (CFTR/MRP), member 4 |
| 204268_at | 0.00523735 | 204268_at S100A2 | S100 calcium binding protein A2 |
| 202566_s_at | 0.00524977 | 202566_s_at SVIL | supervillin |
| 209628_at | 0.00526184 | 209628_at NXT2 | nuclear transport factor 2-like export factor 2 |
| 215307_at | 0.00527662 | 215307_at ZNF529 | zinc finger protein 529 |
| 212145_at | 0.00532128 | 212145_at MRPS27 | mitochondrial ribosomal protein S27 |
| 213630_at | 0.00534208 | 213630_at NACAD | NAC alpha domain containing |
| 219468_s_at | 0.0053612 | 219468_s_at CUEDC1 | CUE domain containing 1 |
| 211087_x_at | 0.00542866 | 211087_x_at MAPK14 | mitogen-activated protein kinase 14 |
| 218972_at | 0.00552662 | 218972_at TTC17 | tetratricopeptide repeat domain 17 |
| 202854_at | 0.00553404 | 202854_at HPRT1 | hypoxanthine phosphoribosyltransferase 1 |
| 210099_at | 0.00557043 | 210099_at ABCA2 | ATP-binding cassette, sub-family A (ABC1), member 2 |
| 214366_s_at | 0.00558176 | 214366_s_at ALOX5 | arachidonate 5-lipoxygenase |
| 214840_at | 0.00558879 | 214840_at TOM1L2 | target of myb1-like 2 (chicken) |
| 201626_at | 0.00559018 | 201626_at INSIG1 | insulin induced gene 1 |
| 202599_s_at | 0.00559145 | 202599_s_at NRIP1 | nuclear receptor interacting protein 1 |
| 209023_s_at | 0.00559707 | 209023_s_at STAG2 | stromal antigen 2 |
| 202426_s_at | 0.00560339 | 202426_s_at RXRA | retinoid X receptor, alpha |
| 217920_at | 0.0056171 | 217920_at MAN1A2 | mannosidase, alpha, class 1A, member 2 |
| 207788_s_at | 0.00562728 | 207788_s_at SORBS3 | sorbin and SH3 domain containing 3 |
| 203446_s_at | 0.00566351 | 203446_s_at OCRL | oculocerebrorenal syndrome of Lowe |
| 218053_at | 0.00566376 | 218053_at PRPF40A | PRP40 pre-mRNA processing factor 40 homolog A (S. cerevisiae) |
| 210618_at | 0.00566623 | 210618_at RAP1GAP | RAP1 GTPase activating protein |
| 201019_s_at 218819_at | 0.00568176 | 201019_s_at EIF1AP1 /// EIF1AX 18/34 | eukaryotic translation initiation factor 1A pseudogene 1 /// eukaryotic translation initiation factor 1A, X-linked |
| 217366_at | 0.00570307 | 217366_at CTNNA1 | catenin (cadherin-associated protein), alpha 1, 102kDa |
| 220281_at | 0.00576101 | 220281_at SLC12A1 | solute carrier family 12 (sodium/potassium/chloride transporters), member 1 |
| 216974_at | 0.00576129 | 216974_at --- | --- |
| 213112_s_at | 0.00576697 | 213112_s_at SQSTM1 | sequestosome 1 |

Figure 12 continued

| | | | |
|---|---|---|---|
| 221704_s_at | 0.00578358 | 221704_s_at VPS37B | vacuolar protein sorting 37 homolog B (S. cerevisiae) |
| 203988_s_at | 0.00579412 | 203988_s_at FUT8 | fucosyltransferase 8 (alpha (1,6) fucosyltransferase) |
| 216427_at | 0.0058094 | 216427_at --- | --- |
| 205336_at | 0.00584045 | 205336_at PVALB | parvalbumin |
| 210244_at | 0.00590435 | 210244_at CAMP | cathelicidin antimicrobial peptide |
| 201928_at | 0.00593008 | 201928_at PKP4 | plakophilin 4 |
| 219754_at | 0.00594178 | 219754_at RBM41 | RNA binding motif protein 41 |
| 219020_at | 0.00610637 | 219020_at HS1BP3 | HCLS1 binding protein 3 |
| 207061_at | 0.00613022 | 207061_at ERN1 | endoplasmic reticulum to nucleus signaling 1 |
| 201454_s_at | 0.00061316 | 201454_s_at NPEPPS | aminopeptidase puromycin sensitive |
| 209131_s_at | 0.0061424 | 209131_s_at SNAP23 | synaptosomal-associated protein, 23kDa |
| 211691_x_at | 0.00620953 | 211691_x_at --- | --- |
| 210034_s_at | 0.0062156 | 210034_s_at RPL5 | ribosomal protein L5 |
| 214347_s_at | 0.00621857 | 214347_s_at DDC | dopa decarboxylase (aromatic L-amino acid decarboxylase) |
| 206516_at | 0.00622263 | 206516_at AMH | anti-Mullerian hormone |
| 216325_x_at | 0.00625493 | 216325_x_at RTEL1 | regulator of telomere elongation helicase 1 |
| 221835_at | 0.00627177 | 221835_at DTX3 | deltex homolog 3 (Drosophila) |
| 203119_at | 0.00628439 | 203119_at CCDC86 | coiled-coil domain containing 86 |
| 222201_s_at | 0.00629972 | 222201_s_at CASP8AP2 | caspase 8 associated protein 2 |
| 205524_s_at | 0.00636007 | 205524_s_at HAPLN1 | hyaluronan and proteoglycan link protein 1 |
| 220516_at | 0.00636329 | 220516_at ZSCAN2 | zinc finger and SCAN domain containing 2 |
| 219447_s_at | 0.00636332 | 219447_s_at SLC35C2 | solute carrier family 35, member C2 |
| 213198_at | 0.00637845 | 213198_at ACVR1B | activin A receptor, type IB |
| 219045_at | 0.0064217 | 219045_at RHOF | ras homolog gene family, member F (in filopodia) |
| | | 19/34 | |
| 204976_s_at | 0.00645214 | 204976_s_at AMMECR1 | Alport syndrome, mental retardation, midface hypoplasia and elliptocytosis chromosomal region gene 1 |
| 214749_s_at | 0.00065532 | 214749_s_at ARMCX6 /// L | armadillo repeat containing, X-linked 6 /// similar to armadillo repeat containing, X-linked 6 |
| 200060_s_at | 0.00657602 | 200060_s_at RNPS1 | RNA binding protein S1, serine-rich domain |
| 216662_at | 0.00659258 | 216662_at MYO7B | myosin VIIB |
| 201662_s_at | 0.00661695 | 201662_s_at ACSL3 | acyl-CoA synthetase long-chain family member 3 |
| 209654_at | 0.00668688 | 209654_at KIAA0947 | KIAA0947 |
| 202032_s_at | 0.00671585 | 202032_s_at MAN2A2 | mannosidase, alpha, class 2A, member 2 |

Figure 12 continued

| | | | |
|---|---|---|---|
| 209795_at | 0.0067223 | 209795_at | CD69 | CD69 molecule |
| 210599_at | 0.00679866 | 210599_at | ZNF614 | zinc finger protein 614 |
| 215838_at | 0.0068031 | 215838_at | LILRA5 | leukocyte immunoglobulin-like receptor, subfamily A (with TM domain), member 5 |
| 218511_s_at | 0.00681922 | 218511_s_at | PNPO | pyridoxamine 5'-phosphate oxidase |
| 203096_s_at | 0.00683327 | 203096_s_at | RAPGEF2 | Rap guanine nucleotide exchange factor (GEF) 2 |
| 203346_s_at | 0.00689045 | 203346_s_at | MTF2 | metal response element binding transcription factor 2 |
| 213724_s_at | 0.00689731 | 213724_s_at | PDK2 | pyruvate dehydrogenase kinase, isozyme 2 |
| 206428_s_at | 0.00689899 | 206428_s_at | ZNF143 | zinc finger protein 143 |
| 217597_x_at | 0.00690909 | 217597_x_at | RAB40B | RAB40B, member RAS oncogene family |
| 206250_x_at | 0.00691356 | 206250_x_at | AVPR1A | arginine vasopressin receptor 1A |
| 218391_at | 0.00694941 | 218391_at | SNF8 | SNF8, ESCRT-II complex subunit, homolog (S. cerevisiae) |
| 207264_at | 0.00697976 | 207264_at | KDELR3 | KDEL (Lys-Asp-Glu-Leu) endoplasmic reticulum protein retention receptor 3 |
| 221773_at | 0.00701609 | 221773_at | ELK3 | ELK3, ETS-domain protein (SRF accessory protein 2) |
| 212780_at | 0.00707488 | 212780_at | SOS1 | son of sevenless homolog 1 (Drosophila) |
| 206222_at | 0.00708854 | 206222_at | TNFRSF10C | tumor necrosis factor receptor superfamily, member 10c, decoy without an intracellular domain |
| 206061_s_at | 0.0070973 | 206061_s_at | DICER1 | dicer 1, ribonuclease type III |
| 213559_s_at | 0.00710288 | 213559_s_at | ZNF467 | Zinc finger protein 467 |
| 219460_s_at | 0.00710349 | 219460_s_at | TMEM127 | transmembrane protein 127 |
| 218441_s_at | 0.00712236 | 218441_s_at | RPAP1 | RNA polymerase II associated protein 1 |
| 210344_at | 0.00713602 | 210344_at | OSBPL7 | oxysterol binding protein-like 7 |
| 208361_s_at | 0.00717807 | 208361_s_at | POLR3D 20/34 | polymerase (RNA) III (DNA directed) polypeptide D, 44kDa |
| 207745_at | 0.00720316 | 207745_at | CABP2 | calcium binding protein 2 |
| 222064_s_at | 0.00720756 | 222064_s_at | AARSD1 | alanyl-tRNA synthetase domain containing 1 |
| 204893_s_at | 0.00724104 | 204893_s_at | ZFYVE9 | zinc finger, FYVE domain containing 9 |
| 201623_s_at | 0.00728223 | 201623_s_at | DARS | aspartyl-tRNA synthetase |
| 205461_at | 0.00732292 | 205461_at | RAB35 | RAB35, member RAS oncogene family |
| 206220_s_at | 0.00733577 | 206220_s_at | RASA3 | RAS p21 protein activator 3 |
| 220582_at | 0.00739433 | 220582_at | --- | --- |
| 202772_at | 0.00740087 | 202772_at | HMGCL | 3-hydroxymethyl-3-methylglutaryl-Coenzyme A lyase |
| 218977_s_at | 0.00741006 | 218977_s_at | TRNAU1AP | tRNA selenocysteine 1 associated protein 1 |
| 203958_s_at | 0.00744598 | 203958_s_at | ZBTB40 | zinc finger and BTB domain containing 40 |
| 220932_at | 0.00744665 | 220932_at | --- | --- |

Figure 12 continued

| Probe ID | p-value | Gene Symbol | Description |
|---|---|---|---|
| 210787_s_at | 0.00745175 | CAMKK2 | calcium/calmodulin-dependent protein kinase kinase 2, beta |
| 212293_at | 0.00747729 | HIPK1 | homeodomain interacting protein kinase 1 |
| 218749_s_at | 0.00748627 | SLC24A6 | solute carrier family 24 (sodium/potassium/calcium exchanger), member 6 |
| 219526_at | 0.00758021 | C14orf169 | chromosome 14 open reading frame 169 |
| 210681_s_at | 0.00759051 | USP15 | ubiquitin specific peptidase 15 |
| 216698_x_at | 0.00762893 | LOC100290716698_x_at | similar to hCG2044651 /// similar to olfactory receptor, family 7, subfamily A, member 17 /// olfactory receptor, family 7, subfamily E, member 18 pseudogene /// olfactory receptor, family 7, subfamily E, member 35 pseudogene /// olfactory receptor, family 7, subfamily E, member 37 pseudogene /// member 47 pseudogene |
| 218337_at | 0.00763243 | FAM160B2 | family with sequence similarity 160, member B2 |
| 212718_at | 0.00764001 | PAPOLA | poly(A) polymerase alpha |
| 208855_s_at | 0.00765408 | STK24 | serine/threonine kinase 24 (STE20 homolog, yeast) |
| 218743_at | 0.00765662 | CHMP6 | chromatin modifying protein 6 |
| 201901_s_at | 0.00770051 | YY1 | YY1 transcription factor |
| 204435_at | 0.00772527 | NUPL1 | nucleoporin like 1 |
| 202172_at | 0.00776341 | VEZF1 | vascular endothelial zinc finger 1 |
| 215875_at | 0.00779436 | --- | --- |
| 203959_s_at | 0.00780832 | ZBTB40 | zinc finger and BTB domain containing 40 |
| 203566_s_at | 0.00785126 | AGL 21/34 | amylo-1, 6-glucosidase, 4-alpha-glucanotransferase |
| 202743_at | 0.00785532 | PIK3R3 | phosphoinositide-3-kinase, regulatory subunit 3 (gamma) |
| 210813_s_at | 0.0078997 | XRCC4 | X-ray repair complementing defective repair in Chinese hamster cells 4 |
| 213443_at | 0.00791612 | TRADD | TNFRSF1A-associated via death domain |
| 218894_s_at | 0.00791714 | MAGOHB | mago-nashi homolog B (Drosophila) |
| 209054_s_at | 0.00793301 | WHSC1 | Wolf-Hirschhorn syndrome candidate 1 |
| 206829_x_at | 0.00793541 | ZNF430 | zinc finger protein 430 |
| 212745_s_at | 0.00795694 | BBS4 | Bardet-Biedl syndrome 4 |
| 210768_x_at | 0.00803599 | TMCO1 | transmembrane and coiled-coil domains 1 |
| 218180_s_at | 0.00803636 | EPS8L2 | EPS8-like 2 |
| 41397_at | 0.0080801 | ZNF821 | zinc finger protein 821 |
| 212997_s_at | 0.00812215 | TLK2 | tousled-like kinase 2 |

Figure 12 continued

| | | | |
|---|---|---|---|
| 205959_at | 0.00815248 | 205959_at | MMP13 | matrix metallopeptidase 13 (collagenase 3) |
| 211332_x_at | 0.00815915 | 211332_x_at | HFE | hemochromatosis |
| 212389_at | 0.00819561 | 212389_at | SBF1 | SET binding factor 1 |
| 216771_at | 0.00822326 | 216771_at | --- | --- |
| 207753_at | 0.00824174 | 207753_at | ZNF304 | zinc finger protein 304 |
| 220742_s_at | 0.00827625 | 220742_s_at | NGLY1 | N-glycanase 1 |
| 204399_s_at | 0.0082763 | 204399_s_at | EML2 | echinoderm microtubule associated protein like 2 |
| 205300_s_at | 0.00829911 | 205300_s_at | SNRNP35 | small nuclear ribonucleoprotein 35kDa (U11/U12) |
| 214030_at | 0.00832433 | 214030_at | CRYBG3 | beta-gamma crystallin domain containing 3 |
| 203111_s_at | 0.00832834 | 203111_s_at | PTK2B | PTK2B protein tyrosine kinase 2 beta |
| 209579_s_at | 0.00834538 | 209579_s_at | MBD4 | methyl-CpG binding domain protein 4 |
| 221830_at | 0.00837144 | 221830_at | RAP2A | RAP2A, member of RAS oncogene family |
| 201121_s_at | 0.00839363 | 201121_s_at | PGRMC1 | progesterone receptor membrane component 1 |
| 219856_at | 0.00840505 | 219856_at | C1orf116 | chromosome 1 open reading frame 116 |
| 204608_at | 0.00843834 | 204608_at | ASL | argininosuccinate lyase |
| 211042_x_at | 0.00844546 | 211042_x_at | MCAM | melanoma cell adhesion molecule |
| 212725_s_at | 0.008456 | 212725_s_at | TUG1 | taurine upregulated 1 (non-protein coding) |
| 219967_at | 0.00852385 | 219967_at | MRM1 | mitochondrial rRNA methyltransferase 1 homolog (S. cerevisiae) |
| 214938_x_at | 0.00854198 | 214938_x_at | HMGB1 | high-mobility group box 1 |
| 208997_s_at | 0.008548 | 208997_s_at | UCP2 | uncoupling protein 2 (mitochondrial, proton carrier) |
| 209146_at | 0.00858225 | 209146_at | SC4MOL 22/34 | sterol-C4-methyl oxidase-like |
| 204621_s_at | 0.00858559 | 204621_s_at | NR4A2 | nuclear receptor subfamily 4, group A, member 2 |
| 208830_s_at | 0.00858657 | 208830_s_at | SUPT6H | suppressor of Ty 6 homolog (S. cerevisiae) |
| 221798_x_at | 0.00859558 | 221798_x_at | --- | --- |
| 203344_s_at | 0.00862045 | 203344_s_at | RBBP8 | retinoblastoma binding protein 8 |
| 218900_at | 0.00864896 | 218900_at | CNNM4 | cyclin M4 |
| 206954_at | 0.00866847 | 206954_at | WIT1 | Wilms tumor upstream neighbor 1 |
| 213729_at | 0.00869707 | 213729_at | PRPF40A | PRP40 pre-mRNA processing factor 40 homolog A (S. cerevisiae) |
| 200658_s_at | 0.00870888 | 200658_s_at | PHB | prohibitin |
| 217551_at | 0.00872494 | 217551_at | LOC441453 | similar to olfactory receptor, family 7, subfamily A, member 17 |
| 218474_s_at | 0.00876184 | 218474_s_at | KCTD5 | potassium channel tetramerisation domain containing 5 |
| 218080_x_at | 0.00876783 | 218080_x_at | FAF1 | Fas (TNFRSF6) associated factor 1 |
| 212368_at | 0.0087699 | 212368_at | ZNF292 | zinc finger protein 292 |
| 206737_at | 0.00877115 | 206737_at | WNT11 | wingless-type MMTV integration site family, member 11 |
| 204701_s_at | 0.00878341 | 204701_s_at | STOML1 | stomatin (EPB72)-like 1 |

Figure 12 continued

| | | | |
|---|---|---|---|
| 213459_at | 0.00878997 | 213459_at | RPL37A | ribosomal protein L37a |
| 209503_s_at | 0.00879376 | 209503_s_at | PSMC5 | proteasome (prosome, macropain) 26S subunit, ATPase, 5 |
| 211423_s_at | 0.00890708 | 211423_s_at | SC5DL | sterol-C5-desaturase (ERG3 delta-5-desaturase homolog, S. cerevisiae)-like |
| 218609_s_at | 0.00890794 | 218609_s_at | NUDT2 | nudix (nucleoside diphosphate linked moiety X)-type motif 2 |
| 201483_s_at | 0.00892532 | 201483_s_at | SUPT4H1 | suppressor of Ty 4 homolog 1 (S. cerevisiae) |
| 201567_s_at | 0.00896199 | 201567_s_at | GOLGA4 | golgi autoantigen, golgin subfamily a, 4 |
| 206040_s_at | 0.00896619 | 206040_s_at | MAPK11 | mitogen-activated protein kinase 11 |
| 201152_s_at | 0.00897682 | 201152_s_at | MBNL1 | muscleblind-like (Drosophila) |
| 203490_at | 0.00902061 | 203490_at | ELF4 | E74-like factor 4 (ets domain transcription factor) |
| 212896_at | 0.00903757 | 212896_at | SKIV2L2 | superkiller viralicidic activity 2-like 2 (S. cerevisiae) |
| 47105_at | 0.00904804 | 47105_at | DUS2L | dihydrouridine synthase 2-like, SMM1 homolog (S. cerevisiae) |
| 202101_s_at | 0.00908895 | 202101_s_at | RALB | v-ral simian leukemia viral oncogene homolog B (ras related; GTP binding protein) |
| 202466_at | 0.0091419 | 202466_at | POLS | polymerase (DNA directed) sigma |
| 200891_s_at | 0.00923108 | 200891_s_at | SSR1 | signal sequence receptor, alpha |
| 200077_s_at | 0.0092323 | 200077_s_at | OAZ1 | ornithine decarboxylase antizyme 1 |
| 204800_s_at | 0.00926794 | 204800_s_at | DHRS12 | dehydrogenase/reductase (SDR family) member 12 |
| 221700_s_at | 0.00929807 | 221700_s_at | UBA52 23/34 | ubiquitin A-52 residue ribosomal protein fusion product 1 |
| 213832_at | 0.00930011 | 213832_at | KCND3 | potassium voltage-gated channel, Shal-related subfamily, member 3 |
| 210396_s_at | 0.00933195 | 210396_s_at | BOLA2 /// LO pseudogene | bolA homolog 2 (E. coli) /// PI-3-kinase-related kinase SMG-1 /// PI-3-kinase-related kinase SMG-1 pseudogene |
| 205327_s_at | 0.00933827 | 205327_s_at | ACVR2A | activin A receptor, type IIA |
| 204672_s_at | 0.00936105 | 204672_s_at | ANKRD6 | ankyrin repeat domain 6 |
| 215233_at | 0.00936404 | 215233_at | JMJD6 | jumonji domain containing 6 |
| 206730_at | 0.00939064 | 206730_at | GRIA3 | glutamate receptor, ionotrophic, AMPA 3 |
| 216582_at | 0.00942683 | 216582_at | POM121L2 | POM121 membrane glycoprotein-like 2 (rat) |
| AFFX-CreX-5_ | 0.00942783 | AFFX-CreX-5_ | --- | --- |
| 218546_at | 0.00943057 | 218546_at | C1orf115 | chromosome 1 open reading frame 115 |
| 211241_at | 0.0094829 | 211241_at | ANXA2P3 | annexin A2 pseudogene 3 |
| 208626_s_at | 0.00949467 | 208626_s_at | VAT1 | vesicle amine transport protein 1 homolog (T. californica) |
| 219154_at | 0.00949671 | 219154_at | TMEM120B | transmembrane protein 120B |
| 219136_s_at | 0.00952174 | 219136_s_at | LMF1 | lipase maturation factor 1 |
| 218962_s_at | 0.00955173 | 218962_s_at | TMEM168 | transmembrane protein 168 |

Figure 12 continued

| Probe ID | p-value | Gene | Description |
|---|---|---|---|
| 219757_s_at | 0.00957708 | C14orf101 | chromosome 14 open reading frame 101 |
| 219993_at | 0.00957964 | SOX17 | SRY (sex determining region Y)-box 17 |
| 204089_x_at | 0.00959042 | MAP3K4 | mitogen-activated protein kinase kinase kinase 4 |
| 221240_s_at | 0.00959749 | B3GNT4 | UDP-GlcNAc:betaGal beta-1,3-N-acetylglucosaminyltransferase 4 |
| 44617_at | 0.0096064 | OGFOD2 | 2-oxoglutarate and iron-dependent oxygenase domain containing 2 |
| 213751_at | 0.00966301 | LRRC68 | leucine rich repeat containing 68 |
| 217411_s_at | 0.00966673 | RREB1 | ras responsive element binding protein 1 |
| 217247_at | 0.00967323 | --- | --- |
| 208641_s_at | 0.00973337 | RAC1 | ras-related C3 botulinum toxin substrate 1 (rho family, small GTP binding protein Rac1) |
| 207726_at | 0.00975775 | ESRRB | estrogen-related receptor beta |
| 220486_x_at | 0.00977566 | TMEM164 | transmembrane protein 164 |
| 205550_s_at | 0.00979153 | BRE | brain and reproductive organ-expressed (TNFRSF1A modulator) |
| 207384_at | 0.0098368 | PGLYRP1 | peptidoglycan recognition protein 1 |
| 218246_at | 0.00984148 | MUL1 | mitochondrial E3 ubiquitin ligase 1 |
| 221315_s_at | 0.00984854 | FGF22 | fibroblast growth factor 22 |
| 217009_at | 0.00985025 | PGK2 | phosphoglycerate kinase 2 |
| 205983_at | 0.00987165 | DPEP1 | dipeptidase 1 (renal) |
| | | 24/34 | |
| 214535_s_at | 0.00991909 | ADAMTS2 | ADAM metallopeptidase with thrombospondin type 1 motif, 2 |
| 215245_x_at | 0.00995405 | FMR1 | fragile X mental retardation 1 |
| 213540_at | 0.00998542 | HSD17B8 | hydroxysteroid (17-beta) dehydrogenase 8 |
| 205619_s_at | 0.00999177 | MEOX1 | mesenchyme homeobox 1 |

Figure 13.
A
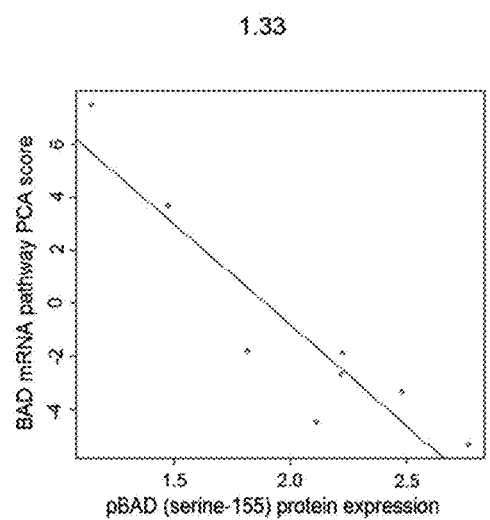
B
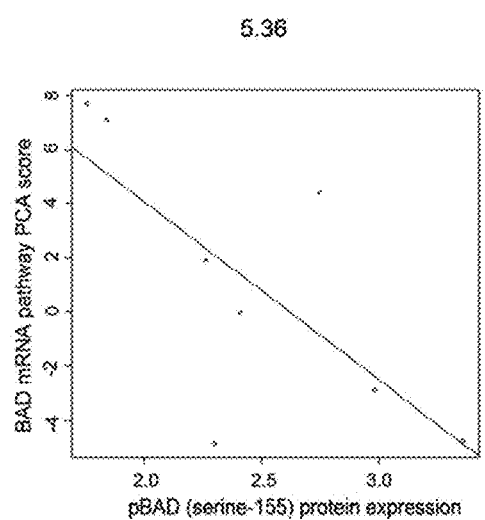

BAD PHOSPHORYLATION DETERMINES OVARIAN CANCER CHEMO-SENSITIVITY AND PATIENT SURVIVAL

CROSS REFERENCE TO RELATED APPLICATION

This application is a continuation of prior filed International Application, Ser. No. PCT/US2012/026617 filed Feb. 24, 2012, which claims priority to U.S. Provisional Patent Application No. 61/446,352, entitled "BAD Phosphorylation Determines Ovarian Cancer Chemo-sensitivity and Patient Survival", filed on Feb. 24, 2011, the contents of which are herein incorporated by reference.

GOVERNMENT SUPPORT STATEMENT

This invention was made with government support under Grant No. CA110499, awarded by the National Cancer Institute and Grant No. W81XWH-08-2-0101, awarded by the United States Army Medical Research and Materiel Command (ARMY/MRMC). The government has certain rights in the invention.

FIELD OF INVENTION

This invention relates to biologic assays. Specifically, the invention provides a method of determining response to clinical treatment of cancer, specifically to chemotherapeutics, and methods of treating chemotherapeutic-resistant cells.

BACKGROUND OF THE INVENTION

Ovarian cancer is the ninth most common cancer, and has the fifth highest mortality for cancers among women in the United States (American Cancer Society Statistics, 2012). As ovarian cancer symptoms tend to develop later in disease progression, most cases are advanced at diagnosis and have spread outside the ovary. Nearly all ovarian cancer patients receive a combination chemotherapy of cisplatin and/or carboplatin. Although the majority of patients with OVCA demonstrate remarkable sensitivity to platinum-based chemotherapy during primary therapy, the majority eventually develop platinum-resistant, recurrent disease (Baker, Salvage therapy for recurrent epithelial ovarian cancer. Hematol Oncol Clin North Am 2003; 17:977-988; Hansen, et al., New cytostatic drugs in ovarian cancer. Ann Oncol 1993; 4 Suppl 4:63-70).

The development of chemoresistance dramatically affects survival for patients with cancer, and as such, targeted therapies that increase chemo-sensitivity offer the potential to significantly improve outcome. The clinical consequences of acquired chemoresistance are exemplified by the high mortality of patients with advanced-stage ovarian cancer (OVCA). Traditionally, resistance can only be determined retrospectively after patients have undergone therapy. Once platinum-resistance has developed, few active therapeutic options exist and patient survival is generally short-lived (Herrin and Thigpen, Chemotherapy for ovarian cancer: current concepts. Semin Surg Oncol 1999; 17:181-188). In this context, platinum resistance is frequently viewed as a surrogate clinical marker for more generic chemoresistance, and it is likely that defining the molecular changes that drive the evolution of the platinum-resistant phenotype will contribute to a broader understanding of human cancer chemoresistance.

Changes in cellular drug efflux, increased cellular glutathione levels, increased DNA repair, and drug tolerance have all been shown to contribute to platinum resistance (Godwin, et al., High resistance to cisplatin in human ovarian cancer cell lines is associated with marked increase of glutathione synthesis. Proc Natl Acad Sci USA 1992; 89:3070-3074; Johnson, et al., Increased platinum-DNA damage tolerance is associated with cisplatin resistance and cross-resistance to various chemotherapeutic agents in unrelated human ovarian cancer cell lines. Cancer Res 1997; 57:850-856; Johnson, et al., Relationship between platinum-DNA adduct formation and removal and cisplatin cytotoxicity in cisplatin-sensitive and -resistant human ovarian cancer cells. Cancer Res 1994; 54:5911-5916). More recently, genomic studies have defined gene expression signatures that may discriminate between cancers that are innately chemo-sensitive versus chemo-resistant (Benedetti, et al., Modulation of survival pathways in ovarian carcinoma cell lines resistant to platinum compounds. Mol Cancer Ther 2008; 7:679-687; Dressman, et al., An integrated genomic-based approach to individualized treatment of patients with advanced-stage ovarian cancer. J Clin Oncol 2007; 25:517-525; Jazaeri, et al., Gene expression profiles associated with response to chemotherapy in epithelial ovarian cancers. Clin Cancer Res 2005; 11:6300-6310). However, the genome-wide expression changes associated with the transition of a cancer cell from chemo-sensitive to chemo-resistant are less clear, and the discrete biologic pathways that drive the process are unknown.

Outcomes for women with ovarian cancer could be improved by the identification of biomarkers capable of identifying resistant tumors and better therapies for treating them. Moreover, how these pathways influence clinical outcomes and their potential as therapeutic targets remain to be defined. As such, improved diagnostics are needed to identify likely chemotherapeutic-resistant cancers and novel targets for therapeutic approaches.

SUMMARY OF THE INVENTION

Few clinical or biologic events impact patient outcome more than response to chemotherapy. A novel in vitro strategy and OVCA model identified the BAD-apoptosis pathway to be influential in the response shown in a range of human cancers to a variety of chemotherapies. Without being bound to any specific theory, BAD appears to function via modulation of BAD phosphorylation. BAD is a member of the BCL2 family of proteins, which are characterized by the presence of up to 4 BCL2-homology domains (Danial and Korsmeyer, Cell death: critical control points. Cell 2004; 116:205-219). This family includes inhibitors and promoters of apoptosis, such that cell survival versus death is determined by the relative ratio of pro-apoptotic (e.g., BCL-Xs, BAD, Bax, Bak) and anti-apoptotic (e.g., Bcl-2, Bcl-xL, MCL-1, A1, BAG-1) family members (Danial and Korsmeyer, Cell death: critical control points. Cell 2004; 116:205-219; Dejean, et al., Oligomeric Bax is a component of the putative cytochrome c release channel MAC, mitochondrial apoptosis-induced channel. Mol Biol Cell 2005; 16:2424-2432; Desagher, et al., Bid-induced conformational change of Bax is responsible for mitochondrial cytochrome c release during apoptosis. J Cell Biol 1999; 144:891-901; Kuwana, et al., Bid, Bax, and lipids cooperate to form supramolecular openings in the outer mitochondrial membrane. Cell 2002; 111:331-342). BAD selectively heterodimerizes with Bcl-xL and Bcl-2 but not with Bax, Bcl-xs, Mcl-1, A1, or itself. When BAD dimerizes with Bcl-xL, Bax is displaced, mitochondrial membrane permeability increases, and apoptosis is induced (Yang, et al., Bad, a heterodimeric partner for Bcl-XL and Bcl-2, displaces Bax and promotes cell death. Cell 1995; 80:285-291). However, BAD function is regulated by phosphorylation (including serine-112, -136, and -155). When phosphorylated, BAD is unable to heterodimerize with Bcl-2 or Bcl-xL, freeing Bcl-xL to dimerize and functionally sequestrate Bax, such that it is no longer free to induce apoptosis (Yang, et al., Bad, a heterodimeric partner for Bcl-XL and Bcl-2, displaces Bax and promotes cell death. Cell 1995; 80:285-291). Thus, the phosphorylation status of BAD determines whether Bax is displaced from Bcl-xL to drive cell death. BAD is thought to be phorphorylated at serine-136 by protein kinase B (PKB/Akt) (del Peso, et al., Interleukin-3-induced phosphorylation of BAD through the protein kinase Akt. Science 1997; 278:687-689). In contrast, serine-112 is phosphorylated by mitogen-activated protein kinase-activated protein kinase-1 (MAPKAP-K1, also called RSK) and PKA. Serine-155, at the center of the BAD BH3 domain, is phosphorylated preferentially by PKA, which also inhibits Bcl-xL binding (Lizcano, et al., Regulation of BAD by cAMP-dependent protein kinase is mediated via phosphorylation of a novel site, Ser155. Biochem J 2000; 349:547-557; Tan, et al., BAD Ser-155 phosphorylation regulates BAD/Bcl-XL interaction and cell survival. J Biol Chem 2000; 275:25865-25869; Zhou, et al., Growth factors inactivate the cell death promoter BAD by phosphorylation of its BH3 domain on Ser155. J Biol Chem 2000; 275:25046-25051). Conversely, the activity of a series of phosphatases, including PP1, PP2A, and PPM1 (PP2C/PPM1A), as well as calcineurin, has been shown to have pro-apoptotic effects via de-phosphorylation of BAD (Klumpp, et al., Protein phosphatase type 2C dephosphorylates BAD. Neurochem Int 2003; 42:555-560; Yang, et al., Calcineurin-mediated BAD Ser155 dephosphorylation in ammonia-induced apoptosis of cultured rat hippocampal neurons. Neurosci Lett 2004; 357:73-75).

The BAD pathway was also identified to be independently associated with clinical outcome for many human cancers. Extensive validation of these findings (and the importance of the BAD pathway) was provided, with in vitro functional studies in addition to in vivo and in silico analyses of >800 patient specimens and/or datasets. Further validation of these findings is provided by the fact that many BAD pathway signature genes, including RAF1, BAD, GNG5, PPM1B, PPM1F, GNAS, PRKAR1A, BAX, PIK3CD, and PTPN11, have previously been reported to be associated with OVCA chemoresponse (Klumpp, et al., Protein phosphatase type 2C dephosphorylates BAD. Neurochem Int 2003; 42:555-560; Yang, et al., Calcineurin-mediated BAD Ser155 dephosphorylation in ammonia-induced apoptosis of cultured rat hippocampal neurons. Neurosci Lett 2004; 357:73-75). Consistently, levels of pBAD were found increased with OVCA cisplatin-resistance in both the cell lines and primary patient samples that were analyzed, and that pBAD protein levels are associated with poor overall survival from ovarian cancer. Further validation of the in vitro and in vivo findings provided by in silico analysis of genomic and chemosensitivity data from 60 cancer cell lines representing 9 tumor types and 8 different chemotherapeutics showed a similar representation of BAD-pathway genes associated with chemosensitivity, suggesting that the pathway may not only influence OVCA cell sensitivity to platinum but also influences many other cancer cell types to a range of different chemotherapeutic agents.

As such, a method of determining clinical outcome or predicting clinical outcome of platinum-based cancer treatment, taxane cancer treatment, gemcitabine, or oxazophorine treatment was developed using a sample of a suspected or known cancer. Non-limiting examples of treatments include the clinical outcome is chemotherapeutic effect, wherein the chemotherapeutic is cisplatin, carboplatin, paclitaxel, gemcitabine, and cyclophosphamide. Further, non-limiting examples of cancers include cancer is ovarian cancer, colon cancers, malignant glioma, breast cancer, leukemia, melanoma, non-small cell lung cancer, central nervous system cancer, renal cancer, and prostate cancer. The phosphorylation level of a BCL2 antagonist of cell death pathway protein was determined in the sample, wherein the BCL2 antagonist of cell death pathway protein is BAD, Bax, BcL-XL, PP2C/PPM1A, AKT, EGFR, IRS-1, Shc, H-Ras, CDK1, G-protein alpha-s, G-protein beta/gamma, PI3K cat class 1A, c-Raf-1, p90Rsk, MEK2 (MAP2K2), PKA-cat, PKA-reg or a combination thereof. Phosphorylation levels may be determined by any means known in the art, including immunofluorescence, Western blot, chip assay, and immunochemistry. The phosphorylation level of a BCL2 antagonist of cell death pathway protein in the sample was then compared to a median level of the phosphorylation level of a BCL2 antagonist of cell death pathway protein, and the responsiveness to treatment determined based on the level of phosphorylation. It is noted that an elevated level of phosphorylation of the BCL2 antagonist of cell death pathway protein in the sample compared to median levels indicates poor clinical outcome to the platinum-based treatment and a reduced level of phosphorylation of the BCL2 antagonist of cell death pathway protein in the sample compared to median levels indicates positive clinical outcome to the platinum-based treatment.

One protein noted for its effect is BCL2 antagonist of cell death phosphorylation, which is optionally compared to median phosphorylated BCL2 antagonist of cell death as a cut-off for high/low categorization. In some variations, the BCL2 antagonist of cell death phosphorylation is detected on serine-112, serine-136, serine-155, or combinations thereof. Low levels of the serine-112 or serine-155 phosphorylation are indicative of superior survival. Alternatively, the BCL2 antagonist of cell death pathway protein is determined in a gene signature, using BAD, Bax, BcL-XL, PP2C/PPM1A, AKT, EGFR, IRS-1, Shc, H-Ras, CDK1, G-protein alpha-s, G-protein beta/gamma, PI3K cat class 1A, c-Raf-1, p90Rsk, MEK2 (MAP2K2), PKA-cat, PKA-reg or a combination thereof; wherein the gene signature is determined by $$\Sigma w_i x_i,$$

where $x_i$ represents gene i expression level and $w_i$ is the corresponding weight (loading coefficient) with $\Sigma w_i^2 = 1$. A BCL2 antagonist of cell death pathway signature score above the median value in all analyses indicates positive clinical outcome to the platinum-based treatment whereas a score below the median indicates poor clinical outcome to the platinum-based treatment.

To support and further explore the clinical relevance of these findings, a 47-gene BAD-pathway signature was developed and evaluated. A panel of OVCA cell lines was subject to serial cisplatin-treatments and the induced cisplatin-resistance was quantified. In parallel, genome-wide expression changes were measured and genes with expression correlated with increasing cisplatin-resistance were analyzed for representation of biologic pathways. In light of the association between cisplatin-resistance and expression of BAD-pathway kinases and phosphatases, levels of phosphorylated-BAD protein were measured in both treated cell lines and also chemo-sensitive and chemo-resistant OVCA patient samples. BAD phosphorylation status was modified in-vitro using targeted siRNA and phosphorylation-site mutagenesis strategies, and the impact on cisplatin-sensitivity measured. Expression of the BAD pathway was studied in a range of cancer cell types and the influence on sensitivity to a variety of chemotherapeutics measured. Finally, a BAD-pathway expression signature was developed and evaluated in treated cell lines and also datasets from 848 patients with a range of different tumor types, which was used to develop a method of determining clinical outcome or predicting clinical outcome of platinum-based cancer treatment, taxane cancer treatment, gemcitabine, or oxazophorine treatment. Non-limiting examples of treatments include chemotherapeutic is cisplatin, carboplatin, paclitaxel, gemcitabine, or cyclophosphamide. A sample of a suspected or known cancer was collected, such as by a biopsy or other means known. Examples of cancers include, without being bound to specific examples, ovarian cancer, colon cancers, malignant glioma, breast cancer, leukemia, melanoma, non-small cell lung cancer, central nervous system cancer, renal cancer, or prostate cancer. The phosphorylation level of a BCL2 antagonist of cell death pathway signature score was determined in the sample using the genes or proteins represented in Table 3, FIG. 5, or FIG. 9, wherein the BCL2 antagonist of cell death pathway signature score is determined by $$\Sigma w_i x_i,$$

where $x_i$ represents gene i expression level and $w_i$ is the corresponding weight (loading coefficient) with $\Sigma w_i^2 =1$; where a BCL2 antagonist of cell death pathway signature score above the median value in all analyses indicates positive clinical outcome to the platinum-based treatment and a score below the median indicates poor clinical outcome to the platinum-based treatment. As discussed above, the phosphorylation level of a BCL2 antagonist of cell death pathway protein level may be detected by means known in the art, such as immunofluorescence. The BCL2 antagonist of cell death pathway signature score is optionally evaluated using a log-rank test.

Testing of the signature in a panel of OVCA cells in which cisplatin-resistance was induced by serial treatments, along with 5 discrete clinical-genomic datasets obtained from 848 patients worldwide; it was demonstrated that a high BAD-pathway signature score is associated with favorable disease-free and/or survival in all tumor types examined. Importantly, analysis of OVCA genomic data and phospho-BAD protein levels from patients with advanced-stage disease suggested that the influence of the BAD pathway on overall survival may be more important than the volume of residual disease at the completion of primary surgery, traditionally one of the most important clinical determinants of outcome for patients with OVCA. Such findings could have substantial implications for future clinical treatment of patients with this disease.

In addition to characterizing a mechanism by which human cancers develop resistance to chemotherapy, a pathway was identified that has significant clinical relevance as a potential biomarker of therapeutic response, overall patient survival, and also as a promising therapeutic target. In vitro manipulation of BAD-phosphorylation levels (by siRNA depletion of a BAD kinase or BAD phosphatase or by targeted mutagenesis of key BAD-phosphorylation sites) resulted in a corresponding change in cisplatin sensitivity, validating the findings and the importance of the BAD pathway. Further validation of the in vitro and in vivo findings is provided by in silico analysis of genomic and chemosensitivity data from 60 cancer cell lines representing 9 tumor types and 8 different chemotherapeutics showed of BAD-pathway genes associated with chemosensitivity, suggesting that the pathway may not only influence OVCA cell sensitivity to platinum but also influences many other cancer cell types to a range of different chemotherapeutic agents. Accordingly, a method of inducing apoptosis in chemotherapeutic-resistant cells was developed. Non-limiting examples of the cancers includes cancer cell is ovarian cancer, colon cancer, malignant glioma, breast cancer, tamoxifen-treated breast cancer, and combinations thereof. A cancer having chemotherapeutic resistance was identified and assayed to determine if the BCL2 antagonist of cell death is phosphorylated. The cancer was then transfected with a plasmid adapted to over-express non-phosphorylated BCL2 antagonist of cell death into a cancer with phosphorylated BCL2 antagonist of cell death, where the non-phosphorylated BCL2 antagonist of cell death causes the chemotherapeutic-resistant cancer cell to undergo apoptosis. In some variations, the non-phosphorylated BCL2 antagonist of cell death is non-phosphorylated BCL2 antagonist of cell death [S136A], non-phosphorylated BCL2 antagonist of cell death [S155A], or combinations thereof. The method is useful for chemotherapeutic-resistant cells to chemotherapeutics, such as carboplatin, paclitaxel, gemcitabine, cyclophosphamide, or cisplatin. In some variations, a chemotherapeutic is administering after the transfection. Examples of the chemotherapeutics includes carboplatin, paclitaxel, gemcitabine, cyclophosphamide, or cisplatin.

BRIEF DESCRIPTION OF THE DRAWINGS

For a fuller understanding of the invention, reference should be made to the following detailed description, taken in connection with the accompanying drawings, in which:

FIG. 12 is a table showing expression data for 397 probesets performed on patient data.

FIGS. 13(A) and (B) is a series of graphs showing high BAD-pathway signature principal component analysis (PCA) score is associated with low expression levels of phosphorylated BAD protein. Scatter plot showing a negative correlation between BAD-pathway signature PCA score and expression levels of phosphorylated BAD (pBAD) (serine-155) protein levels in cell lines generated for cisplatin resistance. (A) Cell lines treated by schedule A. (B) Cell lines treated by schedule C.

DETAILED DESCRIPTION OF THE PREFERRED EMBODIMENT

As used herein, "cancer" refers to the development and growth of abnormal cells in an uncontrolled manner as is commonly understood by those of skill in the art, brought about by aberration of the cellular growth cycle and/or cellular differentiation. Cancers include benign cancers, malignant cancers, and pre-cancerous lesions, as well as both solid tumors and non-solid cancers such as leukemias.

As used herein "platinum-based cancer treatment" or platinum-based chemotherapy" is a drug treatment using compounds having anti-proliferative effects and containing at least one platinum molecule. Exemplary platinum-based compounds include cisplatin, carboplatin, oxaplatin.

As used herein "patient", means members of the animal kingdom, including mammals, such as but not limited to, primates including humans, gorillas and monkeys; rodents, such as mice, fish, reptiles and birds. The patient may be any animal requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

Example 1

Figure 1:
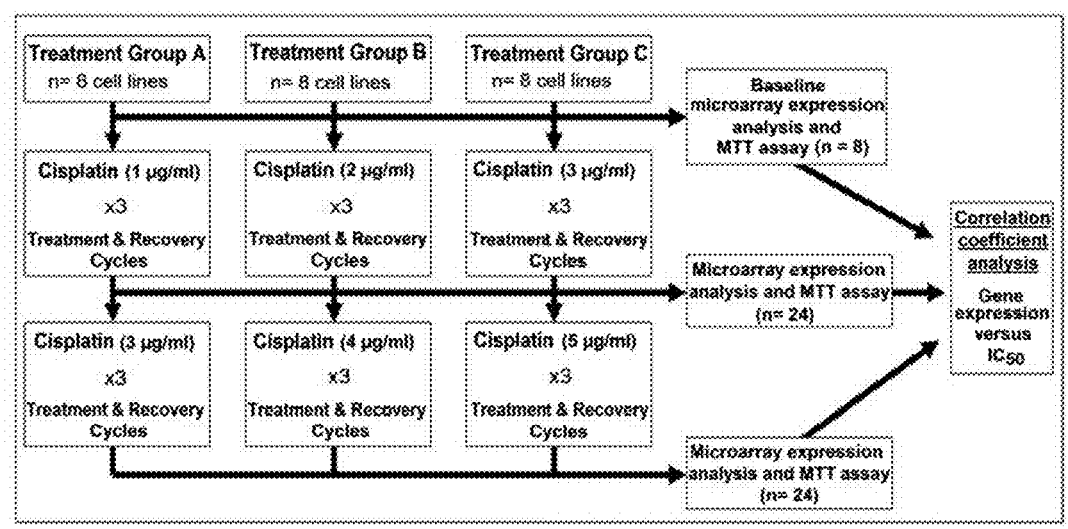
FIG. 1 is a scheme showing the treatment schedule for the in vitro evolution of platinum resistance.

Cell lines were induced for platinum resistance. Acquisition and culture conditions for the expansion of OVCA cells lines (T8, OVCAR5, OV2008, IGROV1, C13, A2780S, A2780CP, and A2008) were reported previously (Boren, et al., MicroRNAs and their target messenger RNAs associated with ovarian cancer response to chemotherapy. Gynecol Oncol 2009; 113:249-255). Cells were subjected to sequential treatment with increasing doses of cis-diammine-dichloroplatinum (cisplatin), using three dosing schedules resulting in 144 treatment/expansion cycles, as seen in FIG. 1. Treatment schedules A, B, and C included three treatments with 1, 2, and 3 µg/mL cisplatin, respectively, followed by three treatments with 3, 4, and 5 µg/mL, respectively. Each cisplatin treatment was followed by a cell recovery/expansion phase. Both cisplatin-resistance and genome-wide expression changes were measured serially in each cell line at baseline and after 3 and 6 cisplatin-treatment/expansion cycles. Cisplatin-resistance was quantified using CellTiter-96 MTS proliferation assays (Thermo Fisher Scientific Inc., Waltham, Mass.) and analyzed genome-wide expression using Affymetrix Human U133 Plus 2.0 GeneChips (Affymetrix, Inc., Santa Clara, Calif.) as previously described (Boren, et al., MicroRNAs and their target messenger RNAs associated with ovarian cancer response to chemotherapy. Gynecol Oncol 2009; 113:249-255; Bild, et al., Oncogenic pathway signatures in human cancers as a guide to targeted therapies. Nature 2006; 439:353-357) (Gene Expression Omnibus (GEO) accession number GSE23553).

Morphologic assessment of condensed chromatin and fragmented DNA quantified percent apoptotic nuclei. Cells were fixed in 4% paraformaldehyde, and nuclei were stained with bis-benzimide trihydrochloride (0.5 µg/ml; Molecular Probes) and quantified using fluorescence microscopy (Marchion, et al., Synergistic interaction between histone deacetylase and topoisomerase II inhibitors is mediated through topoisomerase IIbeta. Clin Cancer Res 2005; 11:8467-8475).

Affymetrix HG-U133A expression and $GI_{50}$ chemosensitivity data for the 60 NCI cancer cell lines (6 leukemia, 9 melanoma, 9 non-small cell lung, 7 colon, 6 central nervous system, 7 ovarian, 8 renal, 2 prostate, and 6 breast cancer cell lines) to cisplatin, carboplatin, cyclophosphamide, doxorubicin, gemcitabine, paclitaxel, docetaxel, and topotecan were obtained from the NCI. For each of the eight drugs, gene expression data from the most sensitive and resistant cell lines (cutoff=mean $GI_{50}$+standard deviation) were compared using an univariate t-test (false discover rate of <20%) (Efron and Tibshirani, Empirical bayes methods and false discovery rates for microarrays. Genet Epidemiol 2002; 23:70-86; Tusher, et al., Significance analysis of microarrays applied to the ionizing radiation response. Proc Natl Acad Sci USA 2001; 98:5116-5121) and subjected to GeneGo/MetaCore™ pathway analyses. The differentially expressed probe sets are shown in Table 1.

TABLE 1

Figure 2:
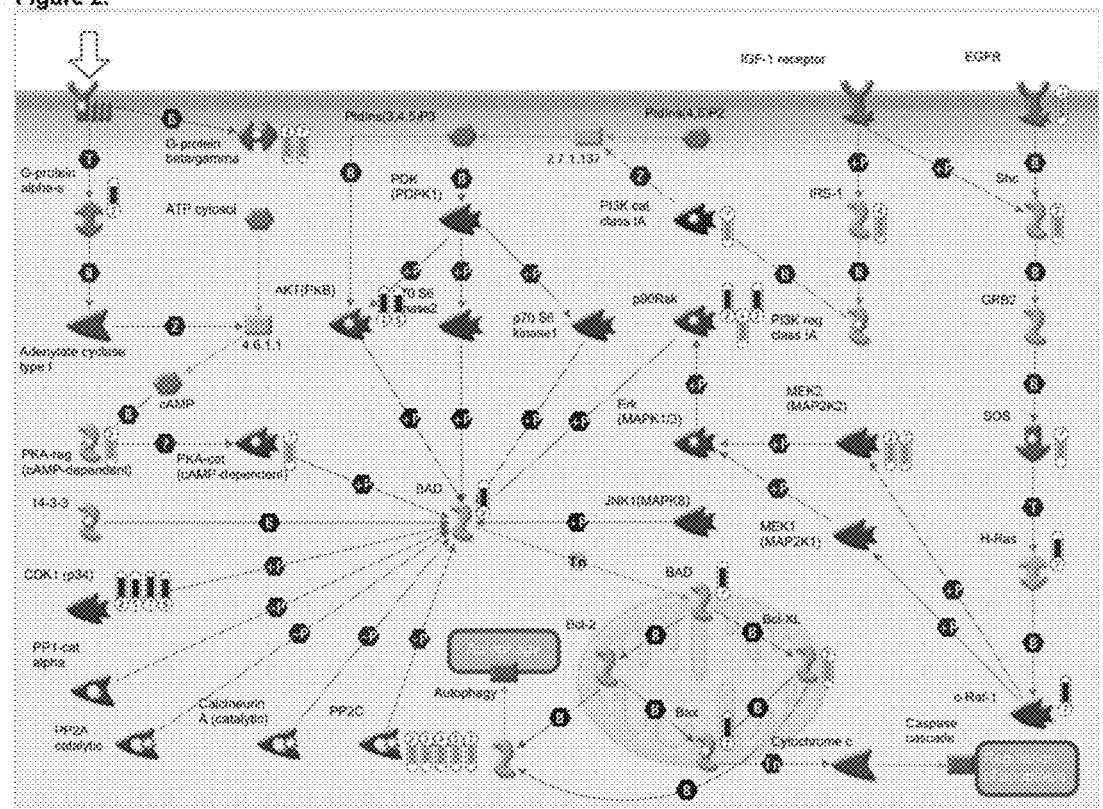
FIG. 2 is an illustration showing the BAD pathway in genes associated with induced cisplatin-resistance. Thermometers indicate those genes that demonstrated a positive (upward pointing) and negative (downward pointing) correlation between expression and increased cisplatin-resistance (EC50) (P<0.001 for pathway enrichment): upward pointing thermometers identify those genes with increasing expression associated with increasing OVCA cisplatin-resistance, and downward pointing thermometers identify those genes with decreasing expression associated with increasing OVCA cisplatin-resistance. Numbers 1-8 at thermometer base identify the cell line (1=T8, 2=OVCAR5, 3=OV2008, 4=IGROV1, 5=C13, 6=A2780S, 7=A2780CP, 8=A2008) that demonstrated changes in expression of that gene with increasing cisplatin-resistance.
Figure 3:
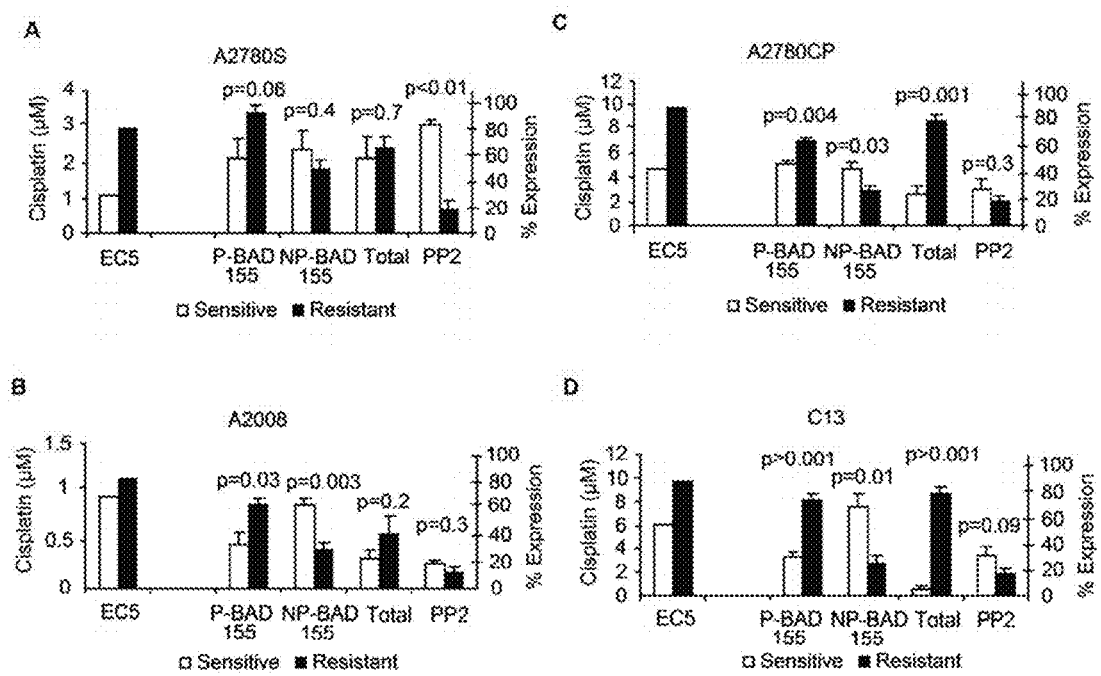
FIGS. 3(A)-(D) are a series of graphs showing BAD-protein phosphorylation is associated with platinum resistance. Cisplatin $EC_{50}$ so results and percent expression of phosphorylated-BAD at serine-155 (P-BAD155), non-phosphorylated BAD (NP-BAD155), total BAD, and PP2C (PPM1A) in (A) A2780S; (B) A2780CP; (C) A2008; and (D) C13 ovarian cancer cell lines measured by MTS and immunofluorescence, respectively.

BAD pathway genes differentially expressed in all NCI60 cancer cell types by drug, related to FIG. 2.

| Probe Set ID | Gene Title | Gene Symbol | up/down |
|---|---|---|---|
| Carboplatin | P < 0.001 | | |
| 213950_s_at | Protein phosphatase 3 (formerly 2B), catalytic subunit, gamma isoform | PPP3CC | down |
| 208743_s_at | tyrosine 3-monooxygenase/tryptophan 5-monooxygenase activation protein, beta polypeptide | YWHAB | up |

TABLE 1-continued

BAD pathway genes differentially expressed in all NCI60 cancer cell types by drug, related to FIG. 2.

| Probe Set ID | Gene Title | Gene Symbol | up/down |
|---|---|---|---|
| 203213_at | cell division cycle 2, G1 to S and G2 to M | CDC2 | up |
| 208652_at | protein phosphatase 2 (formerly 2A), catalytic subunit, alpha isoform | PPP2CA | up |
| 200746_s_at | guanine nucleotide binding protein (G protein), beta polypeptide 1 | GNB1 | down |
| 204566_at | protein phosphatase 1D magnesium-dependent, delta isoform | PPM1D | down |
| 210996_s_at | tyrosine 3-monooxygenase/tryptophan 5-monooxygenase activation protein, epsilon polypeptide | YWHAE | down |
| 200693_at | tyrosine 3-monooxygenase/tryptophan 5-monooxygenase activation protein, theta polypeptide | YWHAQ | down |
| 212249_at | phosphoinositide-3-kinase, regulatory subunit 1 (p85 alpha) | PIK3R1 | down |
| 205867_at | protein tyrosine phosphatase, non-receptor type 11 (Noonan syndrome 1) | PTPN11 | down |
| 204842_x_at | protein kinase, cAMP-dependent, regulatory, type II, alpha | PRKAR2A | up |
| 210317_s_at | tyrosine 3-monooxygenase/tryptophan 5-monooxygenase activation protein, epsilon polypeptide | YWHAE | down |
| 201469_s_at | SHC (Src homology 2 domain containing) transforming protein 1 | SHC1 | up |
| 201983_s_at | epidermal growth factor receptor (erythroblastic leukemia viral (v-erb-b) oncogene homolog, avian) | EGFR | down |
| 210671_x_at | mitogen-activated protein kinase 8 | MAPK8 | up |
| 208478_s_at | BCL2-associated X protein | BAX | down |
| 211833_s_at | BCL2-associated X protein | BAX | down |
| 212271_at | mitogen-activated protein kinase 1 | MAPK1 | down |
| 203777_s_at | ribosomal protein S6 kinase, 70 kDa, polypeptide 2 | RPS6KB2 | up |
| 217575_s_at | Son of sevenless homolog 2 (Drosophila) | SOS2 | up |
| 211551_at | epidermal growth factor receptor (erythroblastic leukemia viral (v-erb-b) oncogene homolog, avian) | EGFR | up |
| 203628_at | insulin-like growth factor 1 receptor | IGF1R | up |
| 209364_at | BCL2-antagonist of cell death | BAD | up |
| 200605_s_at | protein kinase, cAMP-dependent, regulatory, type I, alpha (tissue specific extinguisher 1) | PRKAR1A | up |
| 200638_s_at | tyrosine 3-monooxygenase/tryptophan 5-monooxygenase activation protein, zeta polypeptide | YWHAZ | up |
| 200640_at | tyrosine 3-monooxygenase/tryptophan 5-monooxygenase activation protein, zeta polypeptide | YWHAZ | up |
| 217576_x_at | son of sevenless homolog 2 (Drosophila) | SOS2 | up |
| 201984_s_at | epidermal growth factor receptor (erythroblastic leukemia viral (v-erb-b) oncogene homolog, avian) | EGFR | up |
| 212294_at | guanine nucleotide binding protein (G protein), gamma 12 | GNG12 | up |
| 209296_at | protein phosphatase 1B (formerly 2C), magnesium-dependent, beta isoform | PPM1B | down |
| 203063_at | protein phosphatase 1F (PP2C domain containing) | PPM1F | down |
| 200913_at | protein phosphatase 1G (formerly 2C), magnesium-dependent, gamma isoform | PPM1G | down |
| 213245_at | adenylate cyclase 1 (brain) | ADCY1 | up |
| Cyclophosphamide | P < 0.001 | | |
| 202424_at | mitogen-activated protein kinase kinase 2 | MAP2K2 | up |
| 210407_at | protein phosphatase 1A (formerly 2C), magnesium-dependent, alpha isoform | PPM1A | up |
| 218273_s_at | protein phosphatase 2C, magnesium-dependent, catalytic subunit | PPM2C | up |
| 201020_at | tyrosine 3-monooxygenase/tryptophan 5-monooxygenase activation protein, eta polypeptide | YWHAH | up |
| 204906_at | ribosomal protein S6 kinase, 90 kDa, polypeptide 2 | RPS6KA2 | up |
| 202801_at | protein kinase, cAMP-dependent, catalytic, alpha | PRKACA | down |
| 203627_at | insulin-like growth factor 1 receptor | IGF1R | up |
| 204524_at | 3-phosphoinositide dependent protein kinase-1 | PDPK1 | down |
| 207005_s_at | B-cell CLL/lymphoma 2 | BCL2 | up |
| 212609_s_at | V-akt murine thymoma viral oncogene homolog 3 (protein kinase B, gamma) | AKT3 | down |
| 202457_s_at | protein phosphatase 3 (formerly 2B), catalytic subunit, alpha isoform | PPP3CA | up |

TABLE 1-continued

BAD pathway genes differentially expressed in all NCI60 cancer cell types by drug, related to FIG. 2.

| Probe Set ID | Gene Title | Gene Symbol | up/down |
|---|---|---|---|
| 214227_at | Guanine nucleotide binding protein (G protein), gamma 7 | GNG7 | up |
| 210477_x_at | mitogen-activated protein kinase 8 | MAPK8 | down |
| 212312_at | BCL2-like 1 | BCL2L1 | up |
| 213052_at | Protein kinase, cAMP-dependent, regulatory, type II, alpha | PRKAR2A | up |
| 212240_s_at | phosphoinositide-3-kinase, regulatory subunit 1 (p85 alpha) | PIK3R1 | down |
| 217058_at | GNAS complex locus | GNAS | up |
| 214853_s_at | SHC (Src homology 2 domain containing) transforming protein 1 | SHC1 | down |
| Gemcitabine | p = 0.001 | | |
| 202741_at | protein kinase, cAMP-dependent, catalytic, beta | PRKACB | up |
| 202742_s_at | protein kinase, cAMP-dependent, catalytic, beta | PRKACB | up |
| 202432_at | protein phosphatase 3 (formerly 2B), catalytic subunit, beta isoform | PPP3CB | up |
| 204686_at | insulin receptor substrate 1 | IRS1 | down |
| 203809_s_at | v-akt murine thymoma viral oncogene homolog 2 | AKT2 | up |
| 207124_s_at | guanine nucleotide binding protein (G protein), beta 5 | GNB5 | down |
| 207157_s_at | guanine nucleotide binding protein (G protein), gamma 5 | GNG5 | down |
| 202429_s_at | protein phosphatase 3 (formerly 2B), catalytic subunit, alpha isoform | PPP3CA | up |
| 203214_x_at | cell division cycle 2, G1 to S and G2 to M | CDC2 | down |
| 206896_s_at | guanine nucleotide binding protein (G protein), gamma 7 | GNG7 | down |
| 208351_s_at | mitogen-activated protein kinase 1 | MAPK1 | up |
| 217620_s_at | phosphoinositide-3-kinase, catalytic, beta polypeptide | PIK3CB | up |
| 212912_at | ribosomal protein S6 kinase, 90 kDa, polypeptide 2 | RPS6KA2 | up |
| 204171_at | ribosomal protein S6 kinase, 70 kDa, polypeptide 1 /// similar to ribosomal protein S6 kinase, polypeptide 1 | LOC729334 /// LOC731896 /// RPS6KB1 | down |
| 211578_s_at | ribosomal protein S6 kinase, 70 kDa, polypeptide 1 | RPS6KB1 | down |
| 202743_at | phosphoinositide-3-kinase, regulatory subunit 3 (p55, gamma) | PIK3R3 | up |
| 219393_s_at | v-akt murine thymoma viral oncogene homolog 3 (protein kinase B, gamma) | AKT3 | up |
| Paclitaxel | p = 0.015 | | |
| 203685_at | B-cell CLL/lymphoma 2 | BCL2 | up |
| 200852_x_at | guanine nucleotide binding protein (G protein), beta polypeptide 2 | GNB2 | up |
| 207163_s_at | v-akt murine thymoma viral oncogene homolog 1 | AKT1 | up |
| 207000_s_at | protein phosphatase 3 (formerly 2B), catalytic subunit, gamma isoform | PPP3CC | up |
| 32541_at | protein phosphatase 3 (formerly 2B), catalytic subunit, gamma isoform | PPP3CC | up |
| 215075_s_at | growth factor receptor-bound protein 2 | GRB2 | up |
| 217048_at | — | | up |
| 1861_at | BCL2-antagonist of cell death | BAD | up |
| 209260_at | Stratifin | SFN | up |
| 213699_s_at | tyrosine 3-monooxygenase/tryptophan 5-monooxygenase activation protein, theta polypeptide | YWHAQ | up |
| 222005_s_at | guanine nucleotide binding protein (G protein), gamma 3 | GNG3 | up |
| 200641_s_at | tyrosine 3-monooxygenase/tryptophan 5-monooxygenase activation protein, zeta polypeptide | YWHAZ | up |
| 201375_s_at | protein phosphatase 2 (formerly 2A), catalytic subunit, beta isoform | PPP2CB | up |

To explore the influence of the BAD pathway on the chemosensitivity of several cancer cell types, genomic and chemosensitivity data was evaluated for the 60 NCI cell line panel. Analyzing all cell types together, GeneGo/MetaCore™ identified representations of the BAD pathway in genes differentially expressed in cells sensitive versus those resistant to carboplatin (P≤0.001), paclitaxel (P=0.015), gemcitabine (P=0.001), and cyclophosphamide (P≤0.001) but not to docetaxel, doxorubicin, topotecan, or cisplatin, seen in Table 1. Similarly, this NCI dataset was analyzed by cancer cell type for representation of the BAD pathway associated with sensitivity to individual drugs. Thus, the BAD pathway was found associated with chemosensitivity of OVCA cells to carboplatin (P=0.01), breast cancer cells to carboplatin (P=0.04) and topotecan (P=0.03), leukemia cells to carboplatin and gemcitabine (P=0.03), melanoma cells to paclitaxel (P=0.02), non-small cell lung cancer cells to cyclophosphamide (P=0.02), and colon cancer cells to paclitaxel and docetaxel, seen in Table 2 (P=0.03).

TABLE 2

BAD pathway genes differentially expressed by NCI60 cancer cell types and by drug, related to FIG. 2.

| Probe Set ID | Gene Title | Gene Symbol | up/down |
|---|---|---|---|
| Breast cancer + Carboplatin | p = 0.04 | | |
| 213950_s_at | Protein phosphatase 3 (formerly 2B), catalytic subunit, gamma isoform | PPP3CC | down |
| 208743_s_at | tyrosine 3-monooxygenase/tryptophan 5-monooxygenase activation protein, beta polypeptide | YWHAB | up |
| 203213_at | cell division cycle 2, G1 to S and G2 to M | CDC2 | up |
| 208652_at | protein phosphatase 2 (formerly 2A), catalytic subunit, alpha isoform | PPP2CA | up |
| Breast Cancer + Topotecan | p = 0.03 | | |
| 201984_s_at | epidermal growth factor receptor (erythroblastic leukemia viral (v-erb-b) oncogene homolog, avian) | EGFR | up |
| 206047_at | guanine nucleotide binding protein (G protein), beta polypeptide 3 | GNB3 | down |
| 202742_s_at | protein kinase, cAMP-dependent, catalytic, beta | PRKACB | up |
| 209895_at | protein tyrosine phosphatase, non-receptor type 11 (Noonan syndrome 1) | PTPN11 | up |
| 209896_s_at | protein tyrosine phosphatase, non-receptor type 11 (Noonan syndrome 1) | PTPN11 | up |
| 202429_s_at | protein phosphatase 3 (formerly 2B), catalytic subunit, alpha isoform | PPP3CA | up |
| 200641_s_at | tyrosine 3-monooxygenase/tryptophan 5-monooxygenase activation protein, zeta polypeptide | YWHAZ | up |
| Colon cancer + Paclitaxel | p = 0.03 | | |
| 214853_s_at | SHC (Src homology 2 domain containing) transforming protein 1 | SHC1 | down |
| 204686_at | insulin receptor substrate 1 | IRS1 | down |
| 203685_at | B-cell CLL/lymphoma 2 | BCL2 | up |
| 219393_s_at | v-akt murine thymoma viral oncogene homolog 3 (protein kinase B, gamma) | AKT3 | down |
| 200746_s_at | guanine nucleotide binding protein (G protein), beta polypeptide 1 | GNB1 | down |
| Colon cancer + Docetaxel | p = 0.03 | | |
| 214853_s_at | SHC (Src homology 2 domain containing) transforming protein 1 | SHC1 | up |
| 204686_at | insulin receptor substrate 1 | IRS1 | up |
| 203685_at | B-cell CLL/lymphoma 2 | BCL2 | down |
| 219393_s_at | v-akt murine thymoma viral oncogene homolog 3 (protein kinase B, gamma) | AKT3 | up |
| 200746_s_at | guanine nucleotide binding protein (G protein), beta polypeptide 1 | GNB1 | up |
| Ovarian cancer + Carboplatin | p = 0.01 | | |
| 217575_s_at | Son of sevenless homolog 2 (*Drosophila*) | SOS2 | up |
| 211551_at | epidermal growth factor receptor (erythroblastic leukemia viral (v-erb-b) oncogene homolog, avian) | EGFR | up |
| 203628_at | insulin-like growth factor 1 receptor | IGF1R | up |
| 209364_at | BCL2-antagonist of cell death | BAD | up |
| 200605_s_at | protein kinase, cAMP-dependent, regulatory, type I, alpha (tissue specific extinguisher 1) | PRKAR1A | up |
| 200638_s_at | tyrosine 3-monooxygenase/tryptophan 5-monooxygenase activation protein, zeta polypeptide | YWHAZ | up |
| 200640_at | tyrosine 3-monooxygenase/tryptophan 5-monooxygenase activation protein, zeta polypeptide | YWHAZ | up |

TABLE 2-continued

BAD pathway genes differentially expressed by NCI60 cancer cell types and by drug, related to FIG. 2.

| Probe Set ID | Gene Title | Gene Symbol | up/down |
|---|---|---|---|
| Lung cancer + Cyclophosphamide | p = 0.02 | | |
| 201983_s_at | epidermal growth factor receptor (erythroblastic leukemia viral (v-erb-b) oncogene homolog, avian) | EGFR | up |
| 203627_at | insulin-like growth factor 1 receptor | IGF1R | up |
| 203628_at | insulin-like growth factor 1 receptor | IGF1R | up |
| 204524_at | 3-phosphoinositide dependent protein kinase-1 | PDPK1 | down |
| 207005_s_at | B-cell CLL/lymphoma 2 | BCL2 | up |
| 212609_s_at | V-akt murine thymoma viral oncogene homolog 3 (protein kinase B, gamma) | AKT3 | down |
| Melanoma + Paclitaxel | p = 0.02 | | |
| 202743_at | phosphoinositide-3-kinase, regulatory subunit 3 (p55, gamma) | PIK3R3 | up |
| 207163_s_at | v-akt murine thymoma viral oncogene homolog 1 | AKT1 | up |
| 209296_at | protein phosphatase 1B (formerly 2C), magnesium-dependent, beta isoform | PPM1B | up |
| 207000_s_at | protein phosphatase 3 (formerly 2B), catalytic subunit, gamma isoform | PPP3CC | up |
| 32541_at | protein phosphatase 3 (formerly 2B), catalytic subunit, gamma isoform | PPP3CC | up |
| 210317_s_at | tyrosine 3-monooxygenase/tryptophan 5-monooxygenase activation protein, epsilon polypeptide | YWHAE | down |
| Leukemia + Carboplatin | p = 0.03 | | |
| 201469_s_at | SHC (Src homology 2 domain containing) transforming protein 1 | SHC1 | up |
| 201983_s_at | epidermal growth factor receptor (erythroblastic leukemia viral (v-erb-b) oncogene homolog, avian) | EGFR | down |
| 210671_x_at | mitogen-activated protein kinase 8 | MAPK8 | up |
| 208478_s_at | BCL2-associated X protein | BAX | down |
| 211833_s_at | BCL2-associated X protein | BAX | down |
| 204842_x_at | protein kinase, cAMP-dependent, regulatory, type II, alpha | PRKAR2A | down |
| Leukemia + Gemcitabine | p = 0.03 | | |
| 201469_s_at | SHC (Src homology 2 domain containing) transforming protein 1 | SHC1 | up |
| 201983_s_at | epidermal growth factor receptor (erythroblastic leukemia viral (v-erb-b) oncogene homolog, avian) | EGFR | down |
| 210671_x_at | mitogen-activated protein kinase 8 | MAPK8 | up |
| 208478_s_at | BCL2-associated X protein | BAX | down |
| 211833_s_at | BCL2-associated X protein | BAX | down |
| 204842_x_at | protein kinase, cAMP-dependent, regulatory, type II, alpha | PRKAR2A | down |

BAD-apoptosis pathway proteins, including total BAD, phosphorylated BAD (serine-112,-136, -155), non-phosphorylated BAD (GenScript USA Inc., Piscataway, N.J.), and BAD phosphatase PP2C/PPM1A (Santa Cruz Biotechnology, Inc., Santa Cruz, Calif.), protein levels were evaluated in a subset of the cell line panel (8 cisplatin-treated OVCA cell lines) by Western blot or by immunofluorescence as previously described (Chen, et al., Trophic factor induction of human umbilical cord blood cells in vitro and in vivo. J Neural Eng 2007; 4:130-145; Marchion, et al., Synergistic interaction between histone deacetylase and topoisomerase II inhibitors is mediated through topoisomerase IIbeta. Clin Cancer Res 2005; 11:8467-8475).

OVCA cell lines subjected to serially treated in vitro cisplatin-treatment/expansion cycles demonstrated higher cisplatin $EC_{50}$ values and corresponding higher levels of both pBAD (serine-155) and total BAD than those cells prior to serial cisplatin treatment, as seen in FIGS. 3(A)-(D). In contrast, protein levels of the non-phosphorylated form of BAD (serine-155) and PP2C/PPM1A were expressed at lower levels in serially cisplatin-treated cells. In the OVCA cell lines subjected to serial cisplatin treatment, expression of 3,111 unique probe sets, representing 2,434 unique genes, correlated across dose levels with cisplatin-resistance measured by $EC_{50}$ (Pearson correlation coefficients>0.85, absolute value). GeneGO MetaCore™ (GeneGo, Inc., St. Joseph, Mich.) analysis identified representation of the "BAD phosphorylation, apoptosis and survival" pathway to be associated with development of in vitro cisplatin-resistance, as seen in FIG. 2 (P<0.001). Statistical significance was derived from the number of genes imputed into the analysis software, the number of imputed genes present in a specific pathway, and the actual number of genes in that pathway. Thus, the P value represents the probability that mapping a set of genes to a particular pathway occurs by chance. BAD-pathway genes found to be associated with the evolution of in vitro cisplatin-resistance included BAD, Bax, BcL-XL, PP2C/PPM1A, AKT, EGFR, IRS-1, Shc, H-Ras, CDK1, G-protein alpha-s, G-protein beta/gamma, PI3K cat class 1A, c-Raf-1, p90Rsk, MEK2 (MAP2K2), PKA-cat, and PKA-reg, as seen in FIG. 2.

Figure 4:
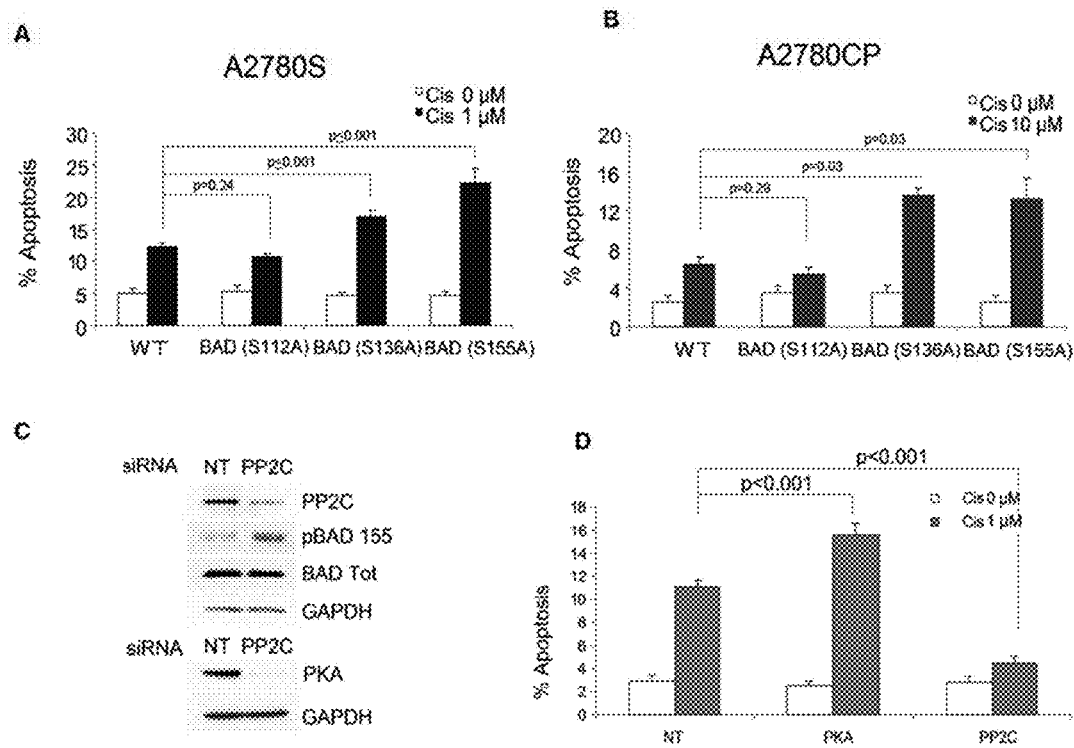
FIGS. 4(A)-(D) is a composite figure showing modulation of BAD-protein phosphorylation status influences cisplatin sensitivity. OVCA cell lines (A) A2780S and (B) A2780CP were transfected with Flag vectors expressing wild-type BAD (WT) or BAD harboring serine (S) to alanine point mutations in serine-112, -136, or -155(S112A, S136A, S155A). These S to A phosphorylation site mutations prevent phosphorylation of the BAD protein. Transfected cells were treated with vehicle or 1 µM (A2780S) or 10 µM (A2780CP) cisplatin for 48 hours and evaluated for the presence of apoptotic nuclei. (C) Western blot showing depletion of PP2C and PKA by siRNA. Controls included a non-targeting siRNA (NT). GAPDH was used as a loading control. (D) Percent apoptotic nuclei in A2780S cells in the presence of 1 µM cisplatin after siRNA depletion of PKA and PP2C. Error bars indicate standard error of the mean.

Many of the BAD-pathway genes found to be associated with evolution of in vitro cisplatin-resistance are known to influence BAD phosphorylation, seen in FIG. 2. The hypothesis that BAD-phosphorylation status is associated with OVCA cisplatin-resistance was then tested. Protein levels of total BAD, phosphorylated BAD (pBAD; serine-112, -136, and -155), the non-phosphorylated form of BAD (serine-155), and the BAD phosphatase PP2C/PPM1A were evaluated by immunofluorescence in 1) OVCA cell lines subjected to serial cisplatin treatment (A2780S, A2780CP, A2008, C13) and 2) 148 primary OVCA samples. Modulation of BAD phosphorylation status influenced cisplatin sensitivity in OVCA cell lines. Over-representation of non-phosphorylated BAD by transfection of A2780S and A2780CP cells with vectors containing serine (S) to alanine (A) mutations (BAD[S136A], BAD[S155A]) in BAD (site mutations that prevent phosphorylation of the BAD protein) resulted in increased cisplatin-induced apoptosis compared to cells transfected with wild-type BAD, as seen in FIGS. 4(A) and (B). In contrast, cells transfected with BAD [S112A] had no effect on cisplatin sensitivity, seen in FIGS. 4(A) and (B).

Cells were transfected with siRNA drawn against different BAD pathway proteins. RNA duplexes for PP2C/PPM1A (s10909 from ABI), cAMP-dependent protein kinase (PKA; 6406 from Cell Signaling Technology, Inc., Danvers, Mass.), and vectors containing mutated BAD (pFlag-600) were transfected using the Nucleofector transfection kit, with non-targeting Silencer negative control #2 siRNA (Applied Biosystems, Inc., Foster City, Calif.), according to manufacturer's protocols (Amaxa GmbH, Koeln, Del.). The role of pBAD (serine-155) in cisplatin sensitivity was further evaluated in A2780S cells by depletion of PKA and PP2C/PPM1A using siRNA. Depletion of PKA and PP2C/PPM1A resulted in reduced target protein expression, seen in FIG. 4(C). Depletion of PKA decreased pBAD levels and increased cisplatin-induced apoptosis compared to cells transfected with a non-targeting control siRNA. In contrast, cells depleted of PP2C/PPM1A demonstrated increased pBAD levels and decreased cisplatin-induced apoptosis, seen in FIGS. 4(C) and (D).

Pearson correlation was used to identify genes associated with OVCA development of cisplatin-resistance ($EC_{50}$). Expression was calculated using the robust multi-array average algorithm (Irizarry, et al., Exploration, normalization, and summaries of high density oligonucleotide array probe level data. Biostatistics 2003; 4:249-264) implemented in Bioconductor (Bioconductor, build number=2.6.2; Fred Hutchinson Cancer Research Center, 2003-2010) extensions to the R-statistical programming environment as described previously (Bolstad, et al., A comparison of normalization methods for high density oligonucleotide array data based on variance and bias. Bioinformatics 2003; 19:185-193). Probe sets with expression ranges<2-fold (maximum/minimum) and control probes (i.e., AFFX_*probe sets) were excluded from the analysis. For each cell line, Pearson correlation coefficients were calculated for expression data and cisplatin $EC_{50}$. Genes/probe sets demonstrating expression/$EC_{50}$ correlations (|R|>0.85) were subjected to biological pathway analysis using GeneGo/MetaCore™ software. Maps/pathways were identified using the GeneGo/MetaCore™ statistical test for significance (P<0.001).

A BAD-pathway gene expression signature was development using a principal component analysis to derive the signature with a corresponding "pathway score" that represents overall gene expression levels for BAD-pathway genes. The signature was evaluated in the panel of OVCA cells previously subject to serial cisplatin-treatments. Specifically, principal component analysis was performed to reduce data dimension into a small set of uncorrelated principal components. This set of principal components was generated based on its ability to account for variation. The first principal component (1st PCA) was used, as it accounts for the largest variability in the data, as a pathway score to represent the overall expression level for the BAD pathway. That is, pathway score=$\Sigma w_i x_i$, a weighted average expression among the BAD pathway genes, where $x_i$ represents gene i expression level, $w_i$ is the corresponding weight (loading coefficient) with $\Sigma w_i^2 = 1$, and the $w_i$ values maximize the variance of $\Sigma w_i x_i$.

Correlations between BAD pathway score and levels of phosphorylated BAD-protein were explored. Based on the above data, a 47-gene BAD-pathway mRNA signature was designed and evaluated, as seen in Table 3.

TABLE 3

BAD pathway signature genes: probesets representing 47 unique genes comprising a BAD-pathway signature, related to FIGS. 4(A)-(D).

| Probe Set ID | Gene Description | Gene Symbol |
|---|---|---|
| 202424_at | mitogen-activated protein kinase kinase 2 | MAP2K2 |
| 213487_at | Mitogen-activated protein kinase kinase 2 | MAP2K2 |
| 213490_s_at | mitogen-activated protein kinase kinase 2 | MAP2K2 |
| 201244_s_at | v-raf-1 murine leukemia viral oncogene homolog 1 | RAF1 |
| 212983_at | v-Ha-ras Harvey rat sarcoma viral oncogene homolog | HRAS |
| 201469_s_at | SHC (Src homology 2 domain containing) transforming protein 1 | SHC1 |
| 214853_s_at | SHC (Src homology 2 domain containing) transforming protein 1 | SHC1 |
| 217048_at | — | — |
| 201983_s_at | epidermal growth factor receptor (erythroblastic leukemia viral (v-erb-b) oncogene homolog, avian) | EGFR |
| 201984_s_at | epidermal growth factor receptor (erythroblastic leukemia viral (v-erb-b) oncogene homolog, avian) | EGFR |

TABLE 3-continued

BAD pathway signature genes: probesets representing 47 unique genes
comprising a BAD-pathway signature, related to FIGS. 4(A)-(D).

| Probe Set ID | Gene Description | Gene Symbol |
| --- | --- | --- |
| 210984_x_at | epidermal growth factor receptor (erythroblastic leukemia viral (v-erb-b) oncogene homolog, avian) | EGFR |
| 211550_at | epidermal growth factor receptor (erythroblastic leukemia viral (v-erb-b) oncogene homolog, avian) | EGFR |
| 211551_at | epidermal growth factor receptor (erythroblastic leukemia viral (v-erb-b) oncogene homolog, avian) | EGFR |
| 211607_x_at | epidermal growth factor receptor (erythroblastic leukemia viral (v-erb-b) oncogene homolog, avian) | EGFR |
| 204686_at | insulin receptor substrate 1 | IRS1 |
| 204369_at | phosphoinositide-3-kinase, catalytic, alpha polypeptide | PIK3CA |
| 212688_at | phosphoinositide-3-kinase, catalytic, beta polypeptide | PIK3CB |
| 217620_s_at | phosphoinositide-3-kinase, catalytic, beta polypeptide | PIK3CB |
| 203879_at | phosphoinositide-3-kinase, catalytic, delta polypeptide | PIK3CD |
| 211230_s_at | phosphoinositide-3-kinase, catalytic, delta polypeptide | PIK3CD |
| 203379_at | ribosomal protein S6 kinase, 90 kDa, polypeptide 1 | RPS6KA1 |
| 204906_at | ribosomal protein S6 kinase, 90 kDa, polypeptide 2 | RPS6KA2 |
| 212912_at | ribosomal protein S6 kinase, 90 kDa, polypeptide 2 | RPS6KA2 |
| 203843_at | ribosomal protein S6 kinase, 90 kDa, polypeptide 3 | RPS6KA3 |
| 1861_at | BCL2-antagonist of cell death | BAD |
| 209364_at | BCL2-antagonist of cell death | BAD |
| 206665_s_at | BCL2-like 1 | BCL2L1 |
| 212312_at | BCL2-like 1 | BCL2L1 |
| 215037_s_at | BCL2-like 1 | BCL2L1 |
| 208478_s_at | BCL2-associated X protein | BAX |
| 211833_s_at | BCL2-associated X protein | BAX |
| 207163_s_at | v-akt murine thymoma viral oncogene homolog 1 | AKT1 |
| 203808_at | — | — |
| 203809_s_at | v-akt murine thymoma viral oncogene homolog 2 | AKT2 |
| 211453_s_at | v-akt murine thymoma viral oncogene homolog 2 | AKT2 |
| 212607_at | v-akt murine thymoma viral oncogene homolog 3 (protein kinase B, gamma) | AKT3 |
| 212609_s_at | V-akt murine thymoma viral oncogene homolog 3 (protein kinase B, gamma) | AKT3 |
| 219393_s_at | v-akt murine thymoma viral oncogene homolog 3 (protein kinase B, gamma) | AKT3 |
| 200744_s_at | guanine nucleotide binding protein (G protein), beta polypeptide 1 | GNB1 |
| 200745_s_at | guanine nucleotide binding protein (G protein), beta polypeptide 1 | GNB1 |
| 200746_s_at | guanine nucleotide binding protein (G protein), beta polypeptide 1 | GNB1 |
| 200852_x_at | guanine nucleotide binding protein (G protein), beta polypeptide 2 | GNB2 |
| 217450_at | — | — |
| 206047_at | guanine nucleotide binding protein (G protein), beta polypeptide 3 | GNB3 |
| 204000_at | guanine nucleotide binding protein (G protein), beta 5 | GNB5 |
| 207124_s_at | guanine nucleotide binding protein (G protein), beta 5 | GNB5 |
| 211871_x_at | guanine nucleotide binding protein (G protein), beta 5 | GNB5 |
| 201921_at | guanine nucleotide binding protein (G protein), gamma 10 /// hypothetical protein LOC552891 | GNG10 /// LOC552891 |
| 204115_at | guanine nucleotide binding protein (G protein), gamma 11 | GNG11 |
| 212294_at | guanine nucleotide binding protein (G protein), gamma 12 | GNG12 |
| 220806_x_at | guanine nucleotide binding protein (G protein), gamma 13 | GNG13 |
| 222005_s_at | guanine nucleotide binding protein (G protein), gamma 3 | GNG3 |
| 205184_at | guanine nucleotide binding protein (G protein), gamma 4 | GNG4 |
| 207157_s_at | guanine nucleotide binding protein (G protein), gamma 5 | GNG5 |
| 206896_s_at | guanine nucleotide binding protein (G protein), gamma 7 | GNG7 |
| 214227_at | Guanine nucleotide binding protein (G protein), gamma 7 | GNG7 |
| 217327_at | — | — |
| 207166_at | guanine nucleotide binding protein (G protein), gamma transducing activity polypeptide 1 | GNGT1 |
| 203966_s_at | protein phosphatase 1A (formerly 2C), magnesium-dependent, alpha isoform | PPM1A |
| 210407_at | protein phosphatase 1A (formerly 2C), magnesium-dependent, alpha isoform | PPM1A |
| 209296_at | protein phosphatase 1B (formerly 2C), magnesium-dependent, beta isoform | PPM1B |
| 213225_at | protein phosphatase 1B (formerly 2C), magnesium-dependent, beta isoform | PPM1B |
| 204566_at | protein phosphatase 1D magnesium-dependent, delta isoform | PPM1D |
| 203063_at | protein phosphatase 1F (PP2C domain containing) | PPM1F |
| 37384_at | protein phosphatase 1F (PP2C domain containing) | PPM1F |

TABLE 3-continued

BAD pathway signature genes: probesets representing 47 unique genes comprising a BAD-pathway signature, related to FIGS. 4(A)-(D).

| Probe Set ID | Gene Description | Gene Symbol |
|---|---|---|
| 200913_at | protein phosphatase 1G (formerly 2C), magnesium-dependent, gamma isoform | PPM1G |
| 218273_s_at | protein phosphatase 2C, magnesium-dependent, catalytic subunit | PPM2C |
| 205867_at | protein tyrosine phosphatase, non-receptor type 11 (Noonan syndrome 1) | PTPN11 |
| 205868_s_at | protein tyrosine phosphatase, non-receptor type 11 (Noonan syndrome 1) | PTPN11 |
| 209895_at | protein tyrosine phosphatase, non-receptor type 11 (Noonan syndrome 1) | PTPN11 |
| 209896_s_at | protein tyrosine phosphatase, non-receptor type 11 (Noonan syndrome 1) | PTPN11 |
| 212610_at | protein tyrosine phosphatase, non-receptor type 11 (Noonan syndrome 1) | PTPN11 |
| 200780_x_at | GNAS complex locus | GNAS |
| 200981_x_at | GNAS complex locus | GNAS |
| 211858_x_at | GNAS complex locus | GNAS |
| 212273_x_at | GNAS complex locus | GNAS |
| 214157_at | GNAS complex locus | GNAS |
| 214548_x_at | GNAS complex locus | GNAS |
| 217057_s_at | GNAS complex locus | GNAS |
| 217058_at | GNAS complex locus | GNAS |
| 217673_x_at | GNAS complex locus | GNAS |
| 200603_at | protein kinase, cAMP-dependent, regulatory, type I, alpha (tissue specific extinguisher 1) | PRKAR1A |
| 200604_s_at | protein kinase, cAMP-dependent, regulatory, type I, alpha (tissue specific extinguisher 1) | PRKAR1A |
| 200605_s_at | protein kinase, cAMP-dependent, regulatory, type I, alpha (tissue specific extinguisher 1) | PRKAR1A |
| 212555_at | protein kinase, cAMP-dependent, regulatory, type I, beta | PRKAR1B |
| 212559_at | protein kinase, cAMP-dependent, regulatory, type I, beta | PRKAR1B |
| 204842_x_at | protein kinase, cAMP-dependent, regulatory, type II, alpha | PRKAR2A |
| 204843_s_at | protein kinase, cAMP-dependent, regulatory, type II, alpha | PRKAR2A |
| 213052_at | Protein kinase, cAMP-dependent, regulatory, type II, alpha | PRKAR2A |
| 203680_at | protein kinase, cAMP-dependent, regulatory, type II, beta | PRKAR2B |
| 203213_at | cell division cycle 2, G1 to S and G2 to M | CDC2 |
| 203214_x_at | cell division cycle 2, G1 to S and G2 to M | CDC2 |
| 210559_s_at | cell division cycle 2, G1 to S and G2 to M | CDC2 |
| 202801_at | protein kinase, cAMP-dependent, catalytic, alpha | PRKACA |
| 216234_s_at | protein kinase, cAMP-dependent, catalytic, alpha /// similar to protein kinase, cAMP-dependent, catalytic, gamma | LOC730418 /// PRKACA |
| 202741_at | protein kinase, cAMP-dependent, catalytic, beta | PRKACB |
| 202742_s_at | protein kinase, cAMP-dependent, catalytic, beta | PRKACB |
| 207228_at | protein kinase, cAMP-dependent, catalytic, gamma | PRKACG |

A BAD-pathway signature score was calculated based on the first principal component to represent the overall expression level for the BAD pathway.

Example 2

Primary OVCA Patient Samples were selected for 1) genome-wide expression data from 142 patients treated at Duke and Moffitt Cancer Centers (including 114, previously reported, Dressman et al. 2007 (Dressman, et al., An integrated genomic-based approach to individualized treatment of patients with advanced-stage ovarian cancer. J Clin Oncol 2007; 25: 517-25), and 28 new samples), and 2) 147 OVCA samples obtained from the University of Minnesota (UMN, n=49) and Moffitt Cancer Center (n=98) and analyzed by immunoflourescence for pBAD protein levels. As such, this study included analysis of data/specimens from 289 (142+148) OVCA patients treated at Moffitt, Duke, and UMN, the characteristics are summarized in Table 4. All 289 patients (including those treated at Moffitt, Duke, UMN) were required to have a pathologically confirmed diagnosis of serous epithelial ovarian cancer, be over 18 years of age, surgically confirmed advanced stage (III/IV) disease, primary surgical cytoreductive surgery prior to chemotherapy, and primary chemotherapy with a platinum-based regimen (±taxane or cyclophosphamide). Further, the samples did not contain non-epithelial cancer, borderline tumors, non-serous tumors, early stage (I/II) disease, absence of pathologic documentation of diagnosis, recurrent disease, receipt of neoadjuvant chemotherapy, or unknown clinical response to primary therapy.

TABLE 4

Summary of the 142 OVCA patients for genomic data

| | | |
|---|---|---|
| average age | | 56 |
| complete responders* | | 101 |
| incomplete responders | | 41 |
| optimal cytoreduction | | 73 |
| suboptimal cytoreduction | | 68 |
| grade | 1 | 6 |
| | 2 | 61 |
| | 3 | 73 |
| | unknown | 2 |

TABLE 4-continued

Summary of the 142 OVCA patients for genomic data

| race | Caucasian | 117 |
|---|---|---|
| | African-American | 18 |
| | Asian | 4 |
| | Hispanic | 1 |
| | unknown | 2 |

*to primary therapy

Using medical record review, overall survival was evaluated and all 289 OVCA samples characterized as CR or incomplete responder (IR) to primary platinum-based therapy using criteria described previously (Dressman, et al., An integrated genomic-based approach to individualized treatment of patients with advanced-stage ovarian cancer. J Clin Oncol 2007; 25: 517-25). Clinical response to primary therapy (surgery plus platinum-based chemotherapy) was therefore established for all 289 patients using standard WHO criteria for patients with measurable disease (Miller, et al., Reporting results of cancer treatment. Cancer 1981; 47: 207-14). CA-125 was used to classify responses only in the absence of a measurable lesion (e.g. patients subject to optimal cytoreductive surgery); CA-125 response criteria were based on established guidelines (Rustin, et al., Use of tumour markers in monitoring the course of ovarian cancer Ann Oncol 1999; 10 Suppl 1: 21-7; Rustin, et al., Defining response of ovarian carcinoma to initial chemotherapy according to serum CA 125. J Clin Oncol 1996; 14: 1545-51). A complete-response (CR) was defined as a complete disappearance of all measurable and assessable disease or, in the absence of measurable lesions, a normalization of the CA-125 level after adjuvant therapy. Patients were considered to have an incomplete-response (IR) if they demonstrated only a partial response, had stable disease, or demonstrated progressive disease during primary therapy. A partial response was considered a 50% or greater reduction in the product obtained from measurement of each bi-dimensional lesion for at least 4 weeks or a decrease in the CA-125 level by at least 50% for at least 4 weeks. Disease progression was defined as a 50% or greater increase in the product from any lesion documented within 8 weeks of initiation of therapy, the appearance of any new lesion within 8 weeks of initiation of therapy, or any increase in the CA-125 from baseline at initiation of therapy. Stable disease was defined as disease not meeting any of the above criteria. All tissues, acquired with Institutional Review Board approval, were processed as previously reported (Dressman, et al., An integrated genomic-based approach to individualized treatment of patients with advanced-stage ovarian cancer. J Clin Oncol 2007; 25: 517-25; Boren, et al., MicroRNAs and their target messenger RNAs associated with ovarian cancer response to chemotherapy. Gynecol Oncol 2009; 113: 249-55). Microarray gene expression data (Affymetrix HG-U133A) were analyzed for 142 patients (114 samples previously reported (4) and 28 Moffitt Cancer Center (MCC) samples; GEO accession number GSE23554).

The role of BAD-pathway mRNA and BAD protein phosphorylation levels was evaluated in chemo-response and/or overall survival in 290 advanced-stage (III/IV) serous epithelial OVCAs, resected at the time of primary surgery from patients who went on to receive platinum-based therapy. All tissues, acquired with Institutional Review Board approval, were processed as previously reported (Dressman, et al., An integrated genomic-based approach to individualized treatment of patients with advanced-stage ovarian cancer. J Clin Oncol 2007; 25:517-525; Boren, et al., MicroRNAs and their target messenger RNAs associated with ovarian cancer response to chemotherapy. Gynecol Oncol 2009; 113:249-255).

Microarray gene expression data (HG-U133A, Affymetrix, Inc., Santa Clara, Calif.) were analyzed for 142 patients, of which 114 samples were previously reported (Dressman, et al., An integrated genomic-based approach to individualized treatment of patients with advanced-stage ovarian cancer. J Clin Oncol 2007; 25:517-525) and 28 samples were obtained from the Moffitt Cancer Center (Tampa, Fla.; GEO accession number GSE23554). The 114 samples were arrayed, and patient data was normalized with the Moffitt Cancer Center data using rma. An R object (as an Expression Set) was created that included the 142 patients with clinical data.

Figure 5:
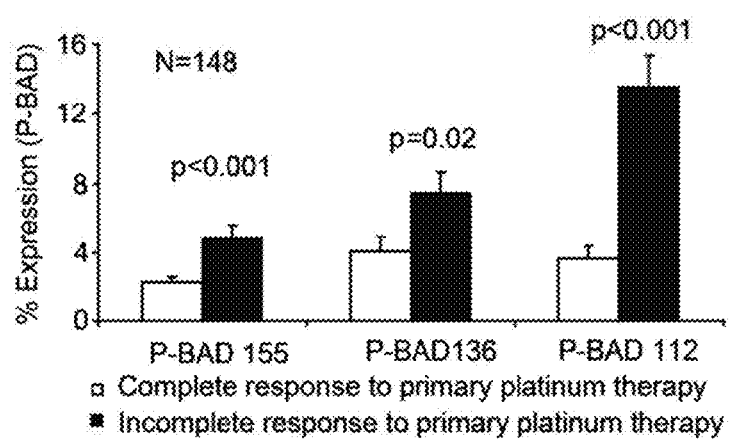
FIG. 5 is a graph showing BAD-protein phosphorylation is associated with platinum resistance. The percent expression of P-BAD at serine-155, -136, and -112 by immunofluorescence in an independent set of 148 primary advanced-stage OVCA samples is shown, including platinum-sensitive/complete responders (CR, n=80) and platinum-resistant/incomplete-responders (IR, n=68). Error bars indicate standard error of the mean.
Figure 6:
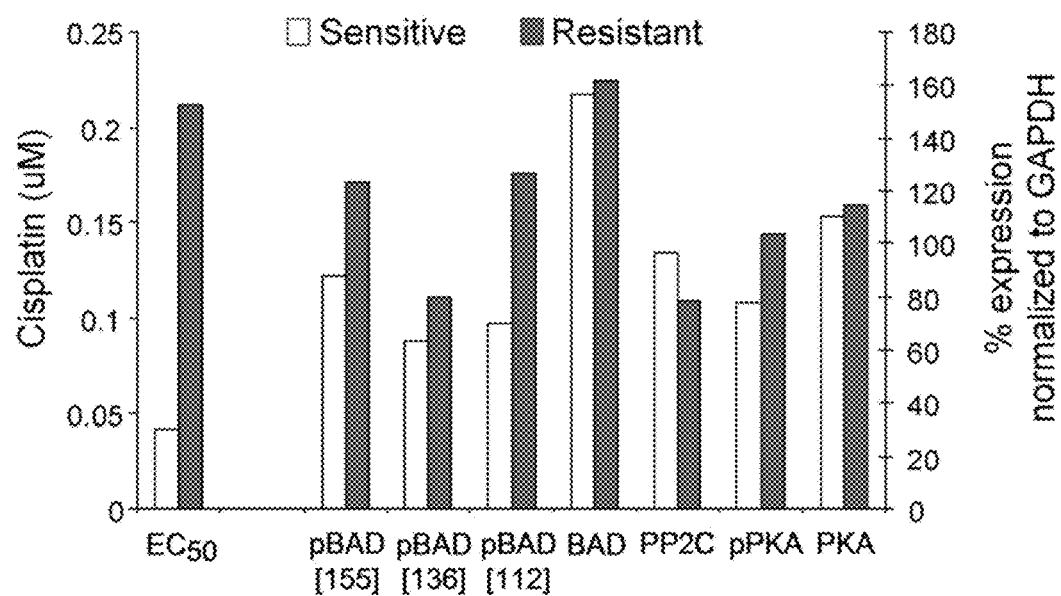
FIG. 6 is a graph showing gene expression levels for chemo-sensitive versus—resistant cell lines exposed to platinum chemotherapeutics.
Figure 7:
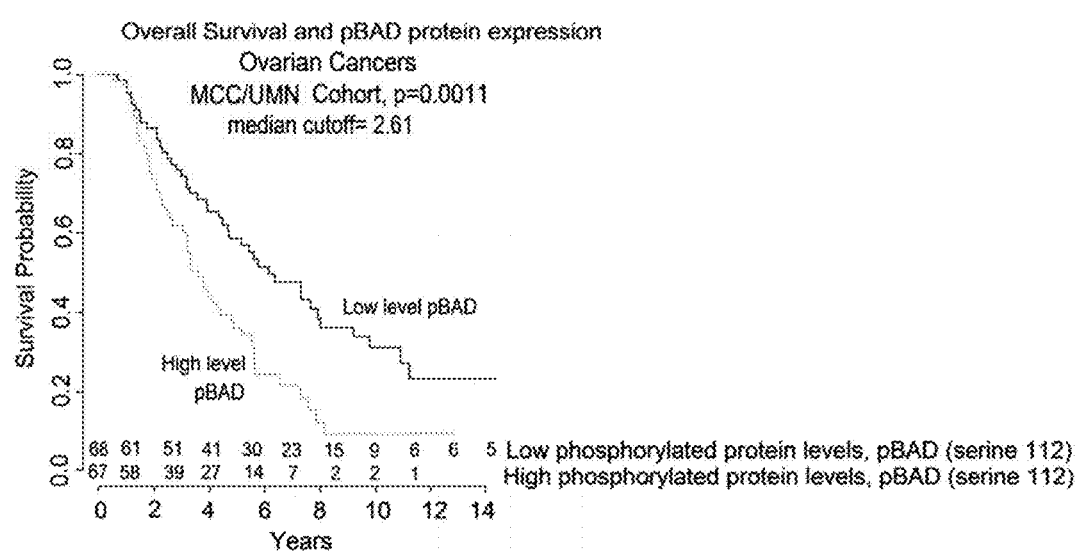
FIG. 7 is a graph showing low expression levels of phosphorylated BAD protein is associated with overall survival. Kaplan-Meier curves depicting the association between the expression levels of phosphorylated BAD (pBAD) (serine-112) protein levels and overall survival from cancer. Panel B: Kaplan-Meier curves showing the association between pBAD (serine-112) levels with Cytoreductive status and overall survival. North American ovarian cancer dataset (*MCC). ˆInformation available for 135 of 142 samples. The numbers at risk are shown at the bottom of graphs. Log-rank test P values indicate significance. O, optimal; S, suboptimal. The median cutoff is 2.61.

An additional 148 primary OVCAs (98 from Moffitt Cancer Center and 50 from University of Minnesota, Duluth, Minn.) were analyzed for BAD-protein levels using immunofluorescence. A summary of the characteristics of the patients is seen in Table 5. Immunofluorescence and BAD protein levels revealed consistently higher levels of pBAD (serine-112, -136, and -155) in platinum-resistant (IR) than in platinum-sensitive (CR) samples (P<0.001, P=0.02, P<0.001, respectively), seen in FIG. 5, as well as slightly higher levels of pPKA and PP2C, as seen in FIG. 6. Using median pBAD as a cut-off for high/low categorization, pBAD (serine-112) levels were independently associated with overall survival. Patients with low levels of pBAD (serine-112) had survival superior to patients with high levels of pBAD (p=0.001), as seen in FIG. 7. When all patients were evaluated, the same trend was observed for patients with low levels of pBAD (serine-155), though the difference did not reach statistical significance (p=0.43). Levels of pBAD (serine-136) were not associated with survival (p=0.897).

TABLE 5

Summary of the 147 OVCA patients for immunoflourescence data

| | | |
|---|---|---|
| average age | | 56 |
| complete responders* | | 86 |
| incomplete responders | | 61 |
| optimal cytoreduction | | 109 |
| suboptimal cytoreduction | | 36 |
| unknown (cytoreduction) | | 2 |
| Mean survival | complete responders | 54 months |
| | incomplete responders | 28 months |

*to primary therapy

Figure 8:
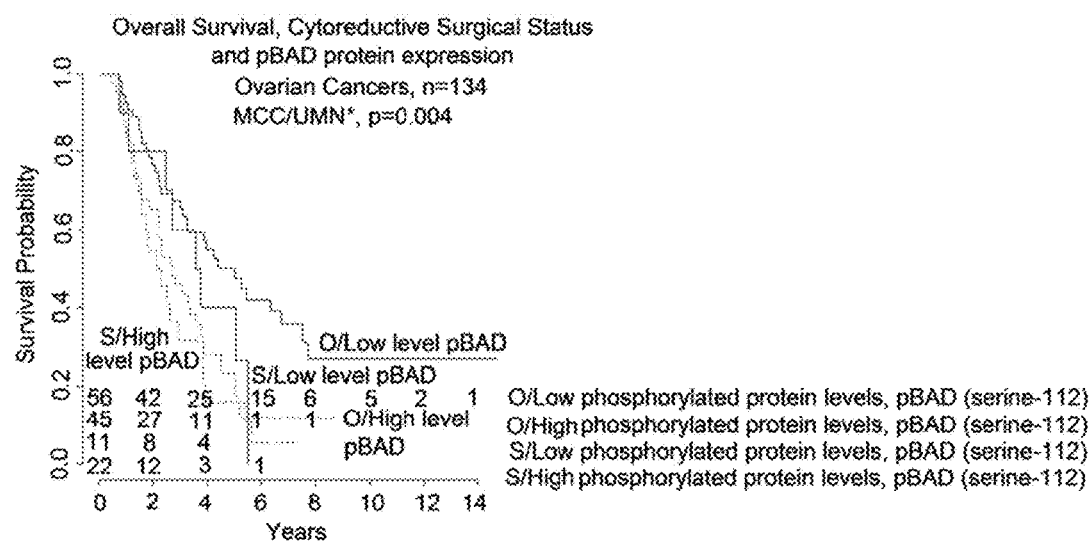
FIG. 8 is a graph showing low expression levels of phosphorylated BAD protein is associated with overall survival. Panel Kaplan-Meier curves showing the association between pBAD (serine-112) levels with Cytoreductive status and overall survival. North American ovarian cancer dataset (*MCC). ˆInformation available for 134 of 142 samples. The numbers at risk are shown at the bottom of graphs. Log-rank test P values indicate significance. O, optimal; S, suboptimal.
Figure 9:
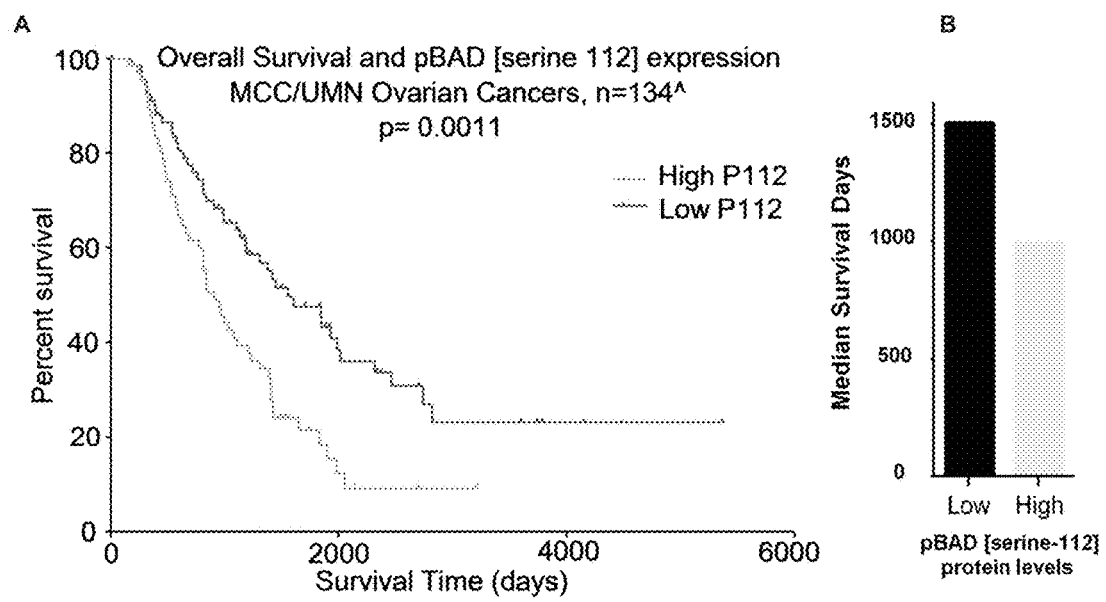
FIG. 9A-B depict a series of graphs showing low phosphorylated [serine 112] BAD is associated with favorable clinical outcome. (A) Kaplan-Meier curves depicting the association between phosphorylated [serine 112] status and overall survival from cancer. The median cutoff is 2.61. (B) Graph depicting low phosphorylated [serine 112] BAD results in increased survival.
Figure 10:
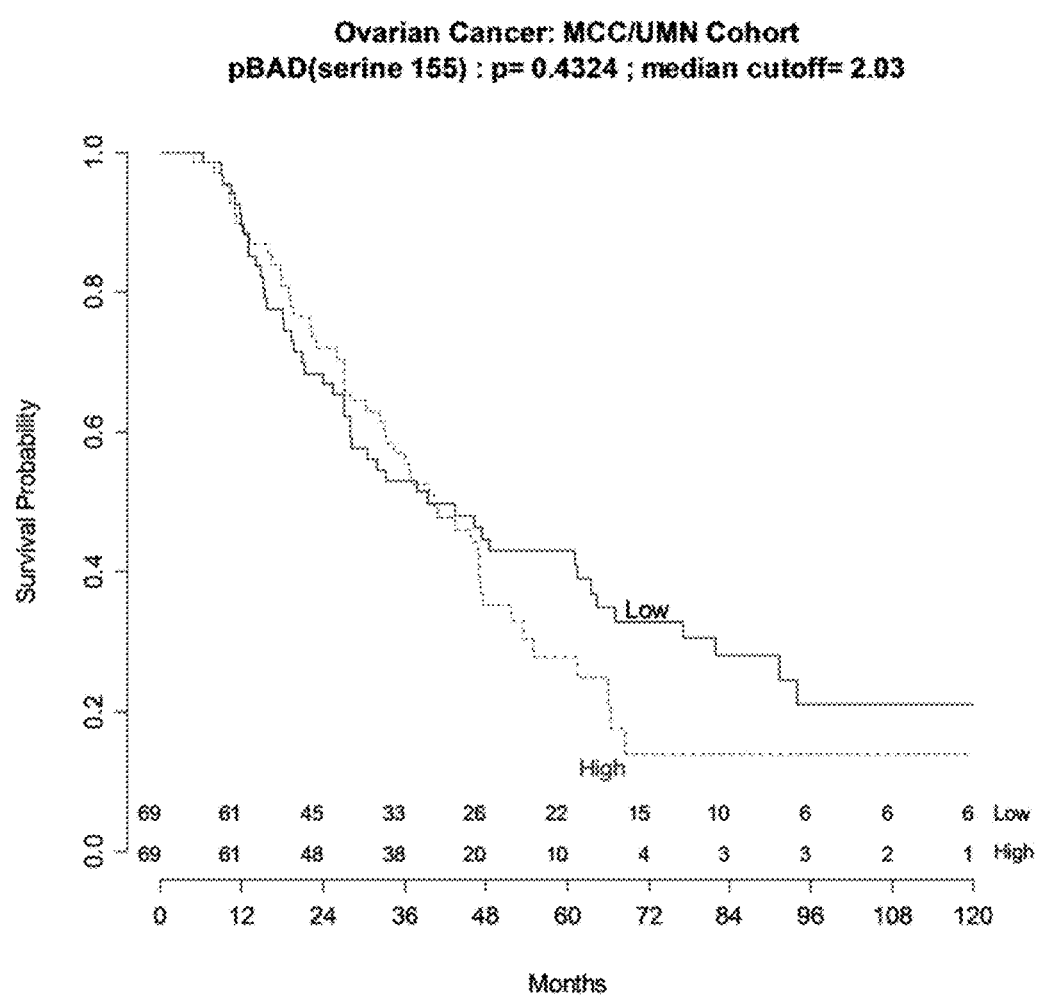
FIG. 10 is a graph showing low phosphorylated [serine 155] BAD is associated with favorable clinical outcome. Kaplan-Meier curves depicting the association between phosphorylated [serine 155] status and overall survival from cancer. The median cutoff is 2.03.
Figure 11:
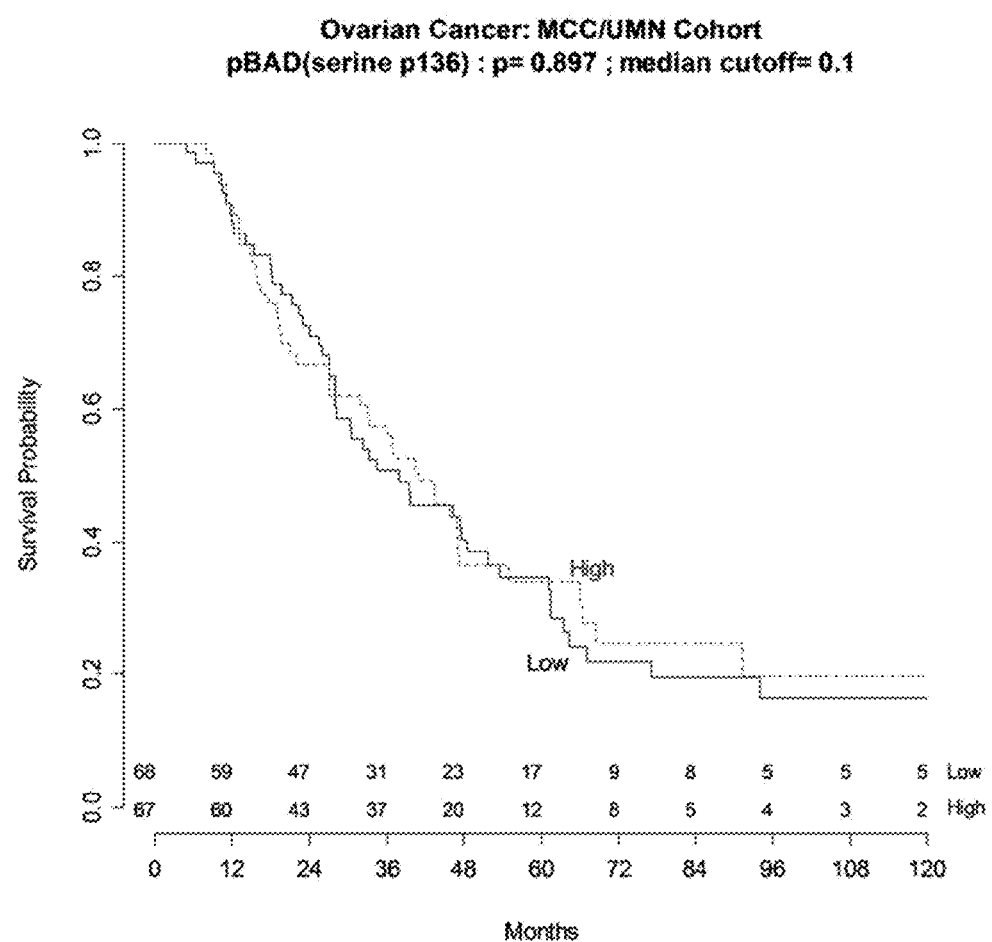
FIG. 11 is a graph showing low phosphorylated [serine 136] BAD is associated with favorable clinical outcome. Kaplan-Meier curves depicting the association between phosphorylated [serine 136] status and overall survival from cancer. The median cutoff is 0.1.
Figure 14:
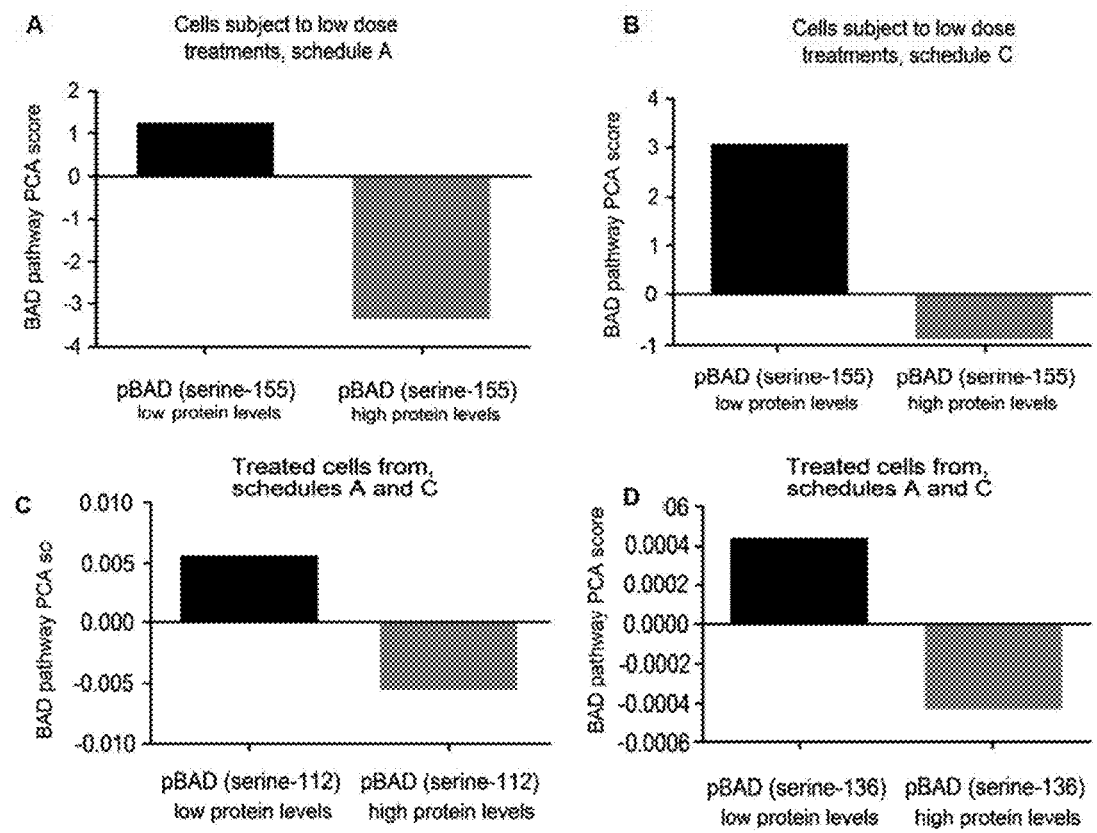
FIGS. 14(A)-(D) are graphs showing the relationship between phosphorylated BAD and BAD pathway PCA scores for (A) phosphorylated serine 155 schedule A, (B) phosphorylated serine 155 schedule C, (C) phosphorylated serine 112 for schedules A and C, and (D) phosphorylated serine 136 for schedules A and C.

Controlling for surgical cytoreductive status and using median pBAD levels as a cut-off, levels of pBAD (serine-112) were independently associated with overall survival, as seen in FIG. 8 (p=0.004). Furthermore, Kaplan Meier survival analysis revealed that patients subject to optimal cytoreductive surgery with low levels of pBAD (serine-112) had superior survival compared to patients who were subject to optimal cytoreductive surgery with high pBAD serine 112, as seen in FIG. 8 (p=0.03). Consistently, although not reaching statistical significance, patients subject to suboptimal cytoreductive surgery with low pBAD (serine-112) levels experienced survival superior to patients subject to suboptimal debulking with high pBAD (serine-112) levels (p=1). Importantly, surgical cytoreduction had no influence on survival for patients with high levels of pBAD (serine-112, p=1; serine-136, p=0.22; serine-155, p=0.7). Total BAD, phosphorylated BAD (serine-112, -136, -155), non-phosphorylated BAD (Genscript), and BAD phosphatase PP2C/PPM1A (Santa Cruz Biotechnology) protein levels were evaluated in primary OVCA patient samples by Western blot or by immunofluorescence as previously described (Chen, et al., Trophic factor induction of human umbilical cord blood cells in vitro and in vivo. J Neural Eng 2007; 4:130-145; Marchion, et al., Synergistic interaction between histone deacetylase and topoisomerase II inhibitors is mediated through topoisomerase IIbeta. Clin Cancer Res 2005; 11:8467-8475), as seen in FIGS. 9 through 11.

Using medical record review, overall survival was evaluated and characterized all 290 OVCA samples as complete responders (CR) or incomplete responders (IR) to primary platinum-based therapy using criteria described previously (Dressman, et al., An integrated genomic-based approach to individualized treatment of patients with advanced-stage ovarian cancer. J Clin Oncol 2007; 25:517-525). There are 101 Complete Responders (CR) and 41 Incomplete Responders (IR). Performing a t test between expression in these two groups yields 397 probesets, representing 347 unique genes that were identified as differentially expressed ($P<0.01$) between CR versus IR primary OVCAs, seen in FIG. 12. Pathway analysis of these 347 unique genes in the ovarian cancer patient samples demonstrated representation of the "BAD-phosphorylation, apoptosis and survival" pathway approaching statistical significance ($P<0.08$).

The BAD-pathway gene expression signature was evaluated in 11 external clinical-genomic expression datasets from 838 patients, including 1) 143 patients with ovarian cancer treated at Moffitt Cancer Center and Duke University Medical Center (North American OVCA dataset), 2) 240 patients with OVCA treated in Melbourne, Australia (Tothill, et al. Novel molecular subtypes of serous and endometrioid ovarian cancer linked to clinical outcome. Clin Cancer Res. 2008; 14:5198-208. GSE9891), 3) 286 patients with breast cancer (Wang, et al., Gene-expression profiles to predict distant metastasis of lymph-node-negative primary breast cancer. Lancet 2005; 365:671-9. GSE2034; Carroll, et al., Genome-wide analysis of estrogen receptor binding sites. Nat Genet 2006; 38:1289-97. GSE2034), 4) 50 patients with malignant gliomas (Nutt, et al., Gene expression-based classification of malignant gliomas correlates better with survival than histological classification. Cancer Res. 2003; 63:1602-7), 5) 182 patients with glioblastoma (Lee, et al., Gene expression analysis of glioblastomas identifies the major molecular basis for the prognostic benefit of younger age. BMC Med Genomics 2008; 1:52. GSE13041), 6) 129 patients with lung cancer (Raponi, et al., Gene expression signatures for predicting prognosis of squamous cell and adenocarcinomas of the lung. Cancer Res. 2006 Aug. 1; 66(15):7466-72. GSE4573), 7) 205 patients with colon cancer treated at Moffitt Cancer Center (Moffitt internal dataset), 8) 33 endometrial samples (Boren, et al., MicroRNAs and their target messenger RNAs associated with endometrial carcinogenesis. Gynecol Oncol 2008110:206-15), 9) 61 breast samples (atypical ductal hyperplasia, ductal carcinoma in situ, and invasive ductal carcinoma) (Ma, et al., Gene expression profiles of human breast cancer progression. Proc Natl Acad Sci USA 2003; 100:5974-79), 10) 197 breast samples (normal, ductal carcinoma in situ, and invasive ductal carcinoma) (Chen, et al., Proliferative genes dominate malignancy-risk gene signature in histologically normal breast tissue. Breast Cancer Res Treat 2010; 119:335-46. GSE10780), and 11) 155 tamoxifen-treated breast cancers (Chanrion, et al., A gene expression signature that can predict the recurrence of tamoxifen-treated primary breast cancer. Clin Cancer Res. 2008; 14:1744-52).

The association between BAD-pathway score (high versus low score based on median BAD-score cutoff) and clinical outcome was evaluated. Kaplan-Meier survival curves were generated, and high/low BAD-pathway score survival differences were evaluated using a log-rank test. For each dataset, expression data were first standardized (i.e., centered at mean and divided by standard deviation) and then PCA implemented to obtain a BAD-pathway score for each subject. The median of the BAD-pathway score was used as a cutoff to form two groups: high BAD pathway score (>median) and low BAD pathway score (<median). Kaplan-Meier survival curves were generated and log-rank test were used to test any significant difference between survival curves.

Figure 15:
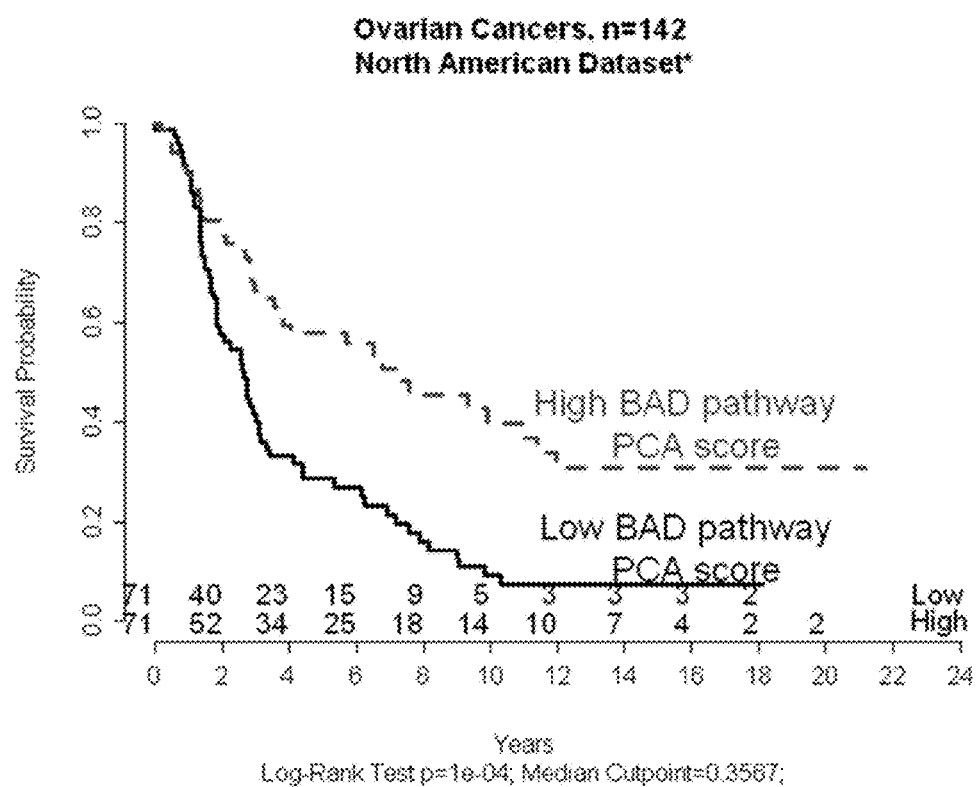
FIG. 15 is a graph showing high BAD-pathway signature principal component analysis (PCA) score is associated with favorable clinical outcome. A Kaplan-Meier curve depicting the association between BAD-pathway signature PCA score and overall survival from cancer for the North American ovarian cancer dataset (*MCC). ˆInformation available for 142 samples. The numbers at risk are shown at the bottom of graphs. Log-rank test P values indicate significance. CR, complete response; IR, incomplete response; O, optimal; S, suboptimal. The median cutoff is 0.3567.
Figure 16:
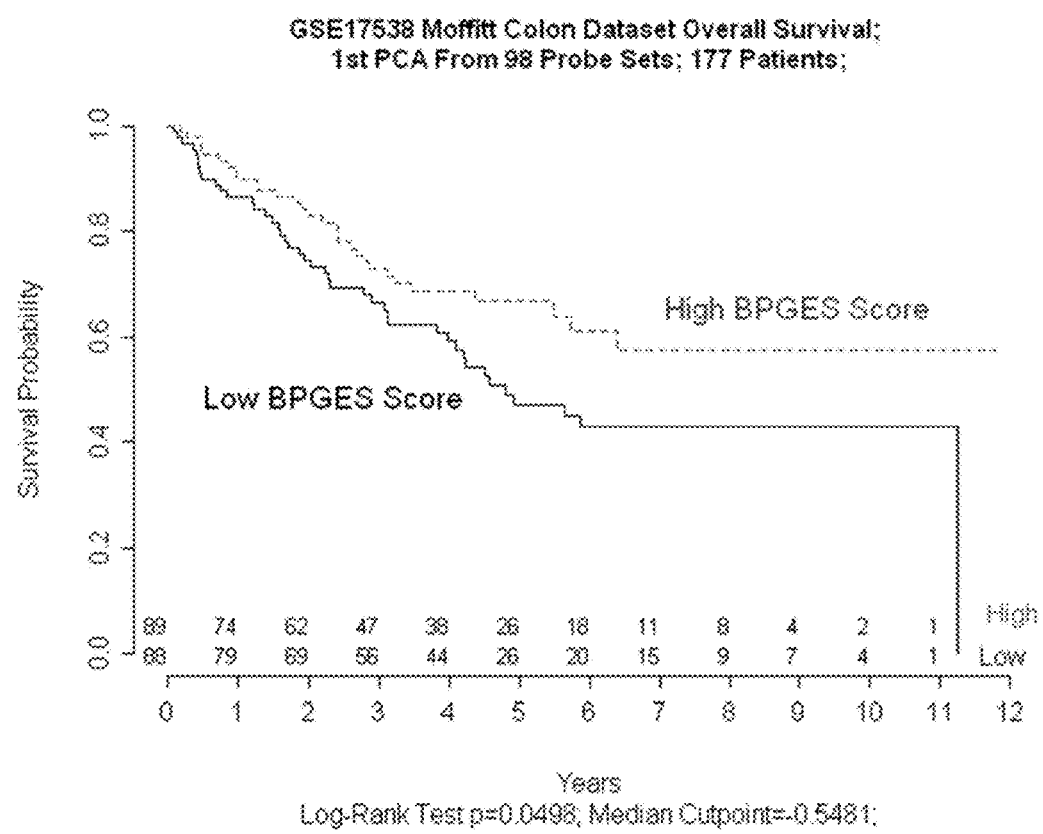
FIG. 16 is a graph showing high BAD-pathway signature principal component analysis (PCA) score is associated with favorable clinical outcome. A Kaplan-Meier curve depicting the association between BAD-pathway signature PCA score and overall survival from a colon cancer dataset (Smith. Et al., (2010) Experimentally derived metastasis gene expression profile predicts recurrence and death in patients with colon cancer. Gastroenterology 138: 958-968.). The numbers at risk are shown at the bottom of graphs. Log-rank test P values indicate significance. CR, complete response; IR, incomplete response; O, optimal; S, suboptimal. The median cutoff is −0.548.
Figure 17:
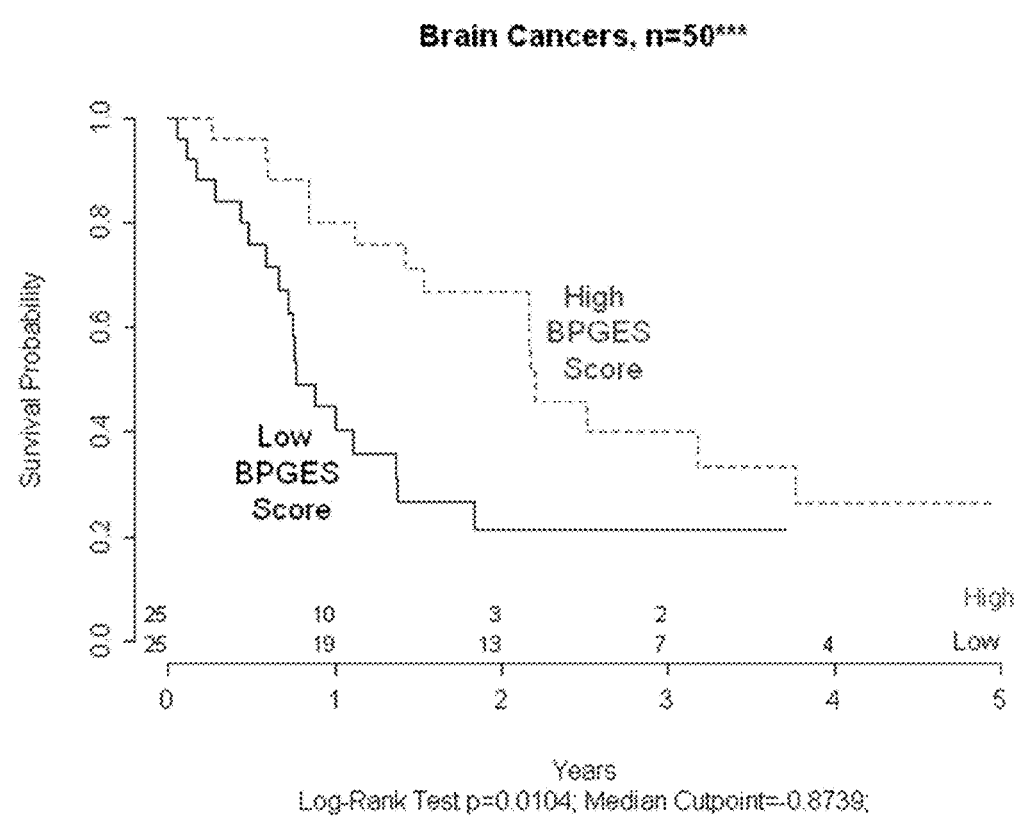
FIG. 17 is a graph showing high BAD-pathway signature principal component analysis (PCA) score is associated with favorable overall clinical outcome. A Kaplan-Meier curve depicting the association between BAD-pathway signature PCA score and overall survival from cancer for the colon cancer dataset (***MCC). #-Nutt, et al., Gene expression-based classification of malignant gliomas correlates better with survival than histological classification. Cancer Res 2003; 63:1602-1607. The numbers at risk are shown at the bottom of graphs. Log-rank test P values indicate significance. CR, complete response; IR, incomplete response; O, optimal; S, suboptimal. The median cutoff is −0.87.
Figure 18:
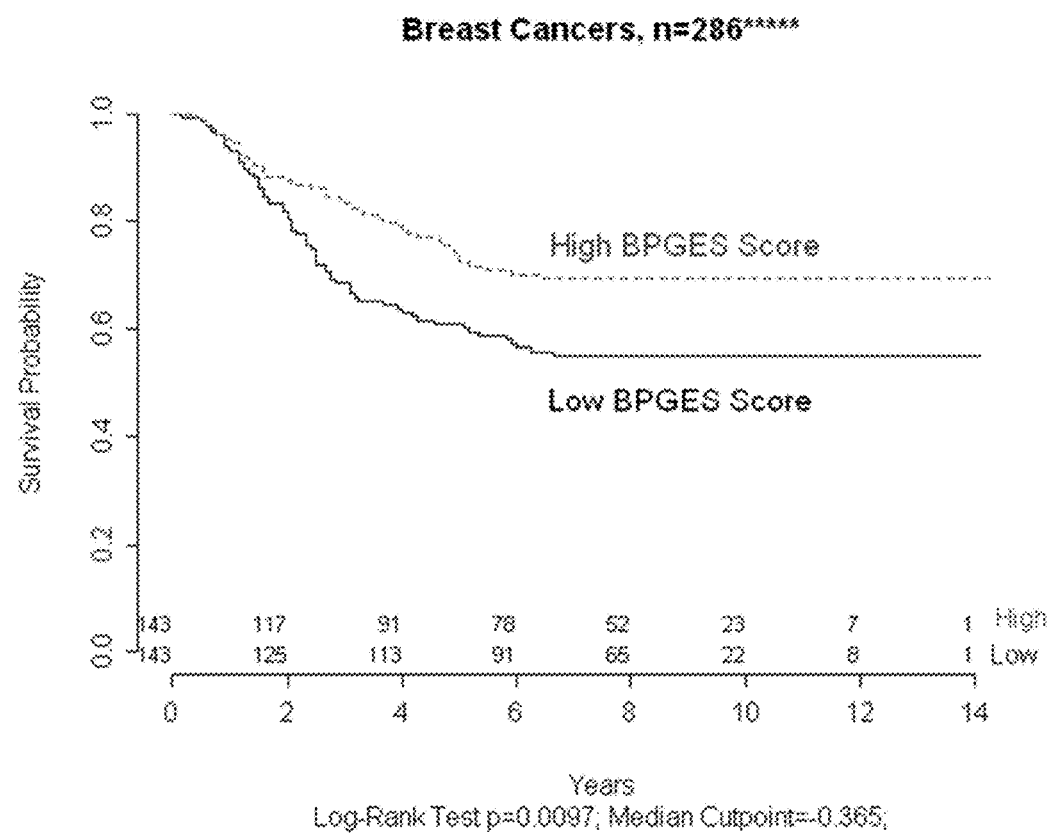
FIG. 18 is a graph showing high BAD-pathway signature principal component analysis (PCA) score is associated with favorable, relapse-free clinical outcome. A Kaplan-Meier curve depicting the association between BAD-pathway signature PCA score and overall survival from a breast cancer dataset (Wang, et al., Gene-expression profiles to predict distant metastasis of lymph-node-negative primary breast cancer. Lancet 2005; 365:671-679). The numbers at risk are shown at the bottom of graphs. Log-rank test P values indicate significance. CR, complete response; IR, incomplete response; O, optimal; S, suboptimal. The median cutoff is −0.365.
Figure 19:
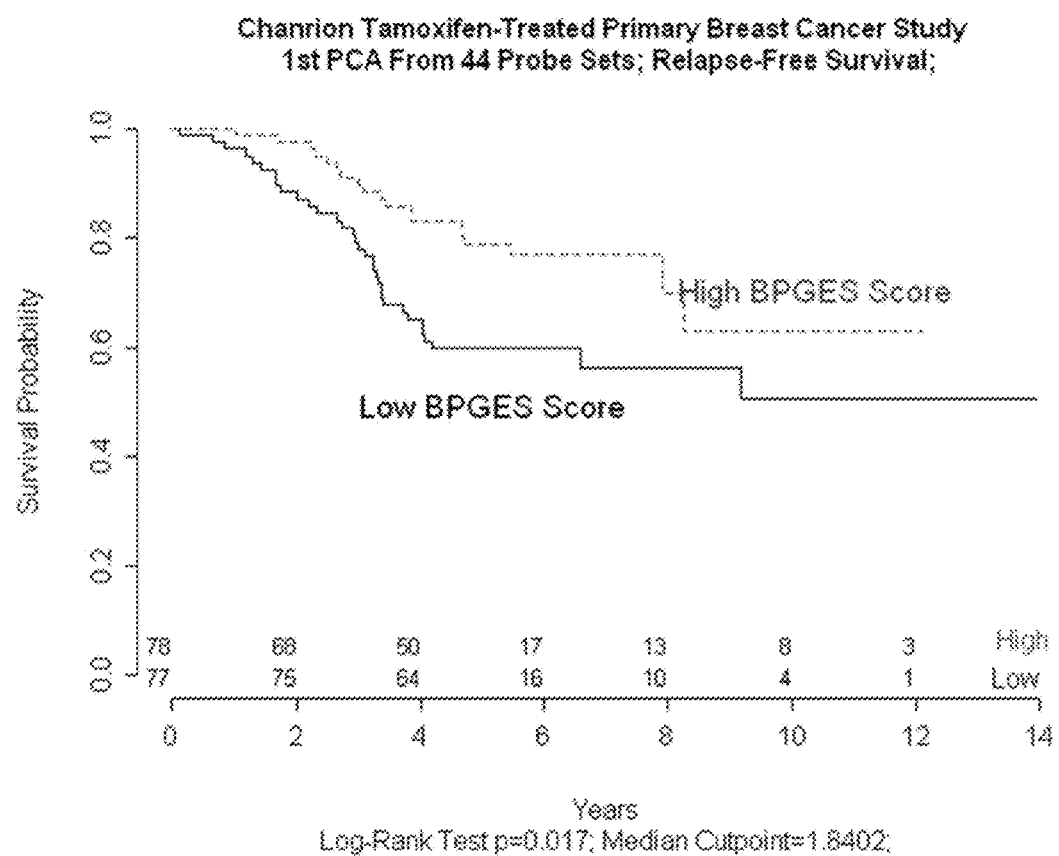
FIG. 19 is a graph showing high BAD-pathway signature principal component analysis (PCA) score is associated with favorable, relapse-free clinical outcome. A Kaplan-Meier curve depicting the association between BAD-pathway signature PCA score and overall survival from cancer for the breast cancer dataset (Chanrion, et al., A gene expression signature that can predict the recurrence of tamoxifen-treated primary breast cancer. Clin Cancer Res 2008; 14:1744-1752). The numbers at risk are shown at the bottom of graphs. Log-rank test P values indicate significance. CR, complete response; IR, incomplete response; O, optimal; S, suboptimal. The median cutoff is 1.84.
Figure 20:
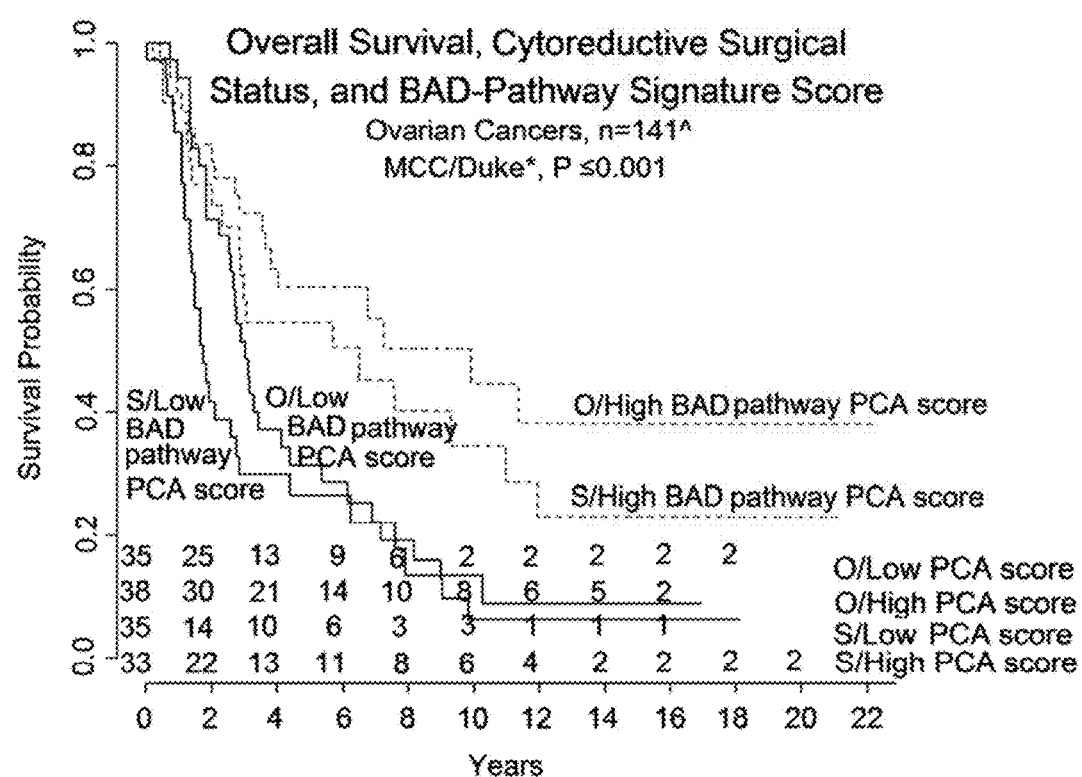
FIG. 20 is a graph showing high BAD-pathway signature principal component analysis (PCA) score is associated with favorable clinical outcome. A Kaplan-Meier curve depicting the association between BAD-pathway signature PCA score and overall survival from cancer for the North American ovarian cancer dataset (*MCC). ^Information available for 141 of 142 samples. The numbers at risk are shown at the bottom of graphs. Log-rank test P values indicate significance. CR, complete response; IR, incomplete response; O, optimal; S, suboptimal.
Figure 21:
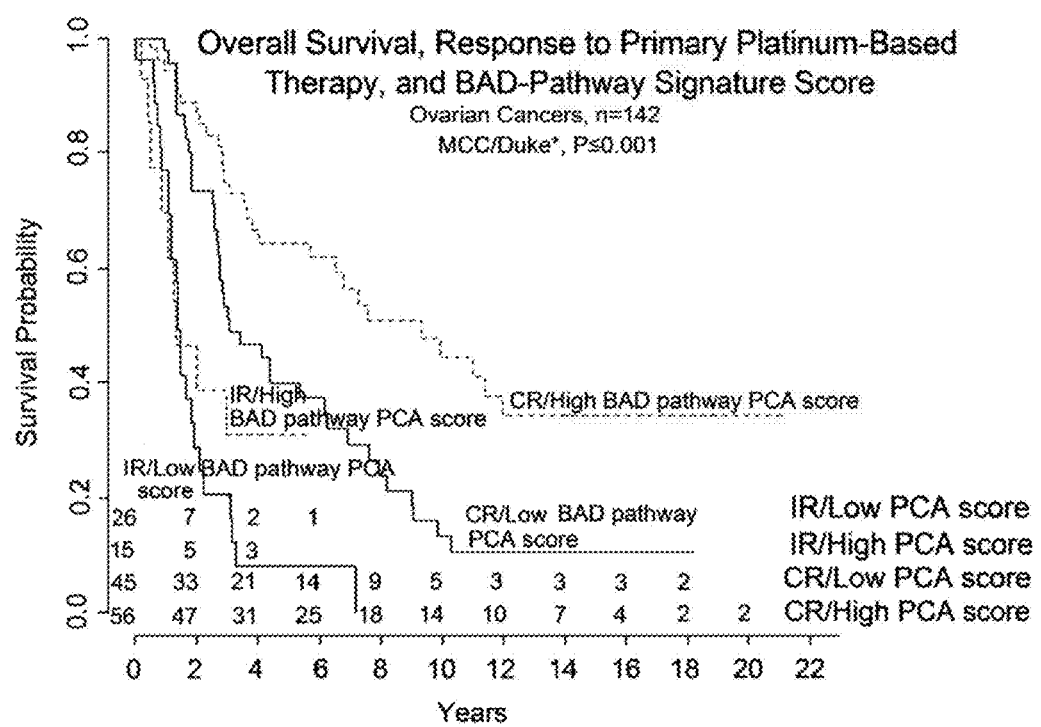
FIG. 21 is a graph showing high BAD-pathway signature principal component analysis (PCA) score is associated with favorable clinical outcome. A Kaplan-Meier curve depicting the association between BAD-pathway signature PCA score and overall survival from cancer for the North American ovarian cancer dataset (*MCC). The numbers at risk are shown at the bottom of graphs. Log-rank test P values indicate significance. CR, complete response; IR, incomplete response; O, optimal; S, suboptimal.

A negative correlation was identified between BAD-pathway score and levels of pBAD (serine-155) protein in cells treated with low-dose cisplatin (schedule A; Pearson score=$-0.8$ p=$0.01$) and higher dose cisplatin (schedule C; Pearson score=$-0.7$ p=$0.07$), as seen in FIGS. 13(A) through 14(D). The BAD-pathway score was associated with overall survival from OVCA, seen in FIG. 15 (n=142, P=0.001), colon cancer, seen in FIG. 16 (n=177, P=0.0498), brain cancer, seen in FIG. 17 (n=50, P=0.01), and relapse-free survival from breast cancer, seen in FIGS. 18 and 19 (2 datasets: n=286, P=0.01; and n=155, P=0.02, respectively). Furthermore, the North American OVCA dataset was evaluated with regard to BAD-pathway score and surgical cytoreductive (debulking) status (optimal: <1 cm; suboptimal: >1 cm residual tumor at conclusion of surgery, seen in FIG. 20 ($P \leq 0.001$) and also response to primary platinum-based therapy, as seen in FIG. 21 (CR or IR, $P \leq 0.001$). The association of high BAD-pathway score and favorable outcome was observed in patients who underwent optimal and suboptimal debulking (optimal: P=0.003, suboptimal: P=0.014). Most importantly, OVCA patients with a high BAD-pathway score who underwent suboptimal debulking had a survival that trended toward superiority compared to patients with a low BAD-pathway score who underwent optimal debulking (P=0.064). Similarly, patients who demonstrated an IR to primary platinum-based therapy but had a high BAD-pathway score had a survival equivalent to those patients who demonstrated a CR but had a low BAD-pathway score (P=0.684). When evaluated with debulking status and response to primary platinum-based therapy, grade, and age, the BAD-pathway score was an independent variable associated with survival (P=0.018).

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a method of determining response to clinical treatment of cancer using platinum-based chemotherapeutics, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating cancer in a patient in need thereof with platinum-based cancer treatment, taxane cancer treatment, gemcitabine, or oxazophorine treatment, comprising;
    determining clinical outcome or predicting clinical outcome of platinum-based cancer treatment, taxane cancer treatment, gemcitabine, or oxazophorine treatment comprising the steps of:
        obtaining a sample of a suspected or known cancer from the patient;
        measuring phosphorylation level of at least one two of a plurality of BAD pathway proteins in the sample by a method selected from the group consisting of immunofluorescence, Western blot, chip assay and immunochemistry;
            wherein the BAD pathway proteins are selected from the group consisting of BAD, Bax, BcL-XL, PP2C/PPM1A, AKT, EGFR, IRS-1, Shc, H-Ras, CDK1, G-protein alpha-s, G-protein beta/gamma, PI3K cat class 1A, c-Raf-1, p90Rsk, MEK2 (MAP2K2), PKA-cat, PKA-reg, and a combination thereof;
        generating a BCL2 antagonist of cell death pathway signature score for the sample of the patient using average expression of the phosphorylation levels among the plurality of BAD pathway proteins using formula $\Sigma w_i x_i$, where $x_i$, represents gene i expression level and $w_i$, is the corresponding loading coefficient with $\Sigma w^2 i=1$;
        calculating a median BCL2 antagonist of cell death pathway signature score using a highest value and a lowest value of the phosphorylation levels of the plurality of BAD pathway proteins measured in the sample;
        determining the patient has a BCL2 antagonist of cell death pathway signature score above the median BCL2 antagonist of cell death pathway signature score by comparing the patient's BCL2 antagonist of cell death pathway signature score to the median BCL2 antagonist of cell death pathway signature score wherein low phosphorylation level is correlated to a higher BCL2 antagonist of cell death pathway signature score;
        wherein a BCL2 antagonist of cell death pathway signature score above the median BCL2 antagonist of cell death pathway score indicates positive clinical outcome to the treatment; and
    administering the platinum-based cancer treatment, taxane cancer treatment, gemcitabine, or oxazophorine treatment to the patient having the BCL2 antagonist of cell death pathway signature score above the median value.

2. The method of claim 1, wherein the phosphorylation level is determined using immunofluorescence.

3. The method of claim 1, wherein the phosphorylation level of BAD protein is measured as one of the at least two of the plurality of BAD proteins.

4. The method of claim 3, wherein the phosphorylation level of BAD is detected on at least one amino acid selected from the group consisting of serine-112, serine-136, serine-155, or combinations thereof.

5. The method of claim 4, wherein the phosphorylation of BAD is compared to median phosphorylation level of BAD as a cut-off for high/low categorization wherein the median phosphorylation level of BAD is about 2.61 for serine-112, about 2.03 for serine-115 or about 0.1 for serine-136.

6. The method of claim 5, wherein levels of the serine-112 or serine-155 phosphorylation that are lower than the median phosphorylation value are indicative of superior survival.

7. The method of claim 1, wherein the BCL2 antagonist of cell death pathway signature is a combination of BAD, Bar, BcL2L, BAX, PP2C/PPM1A, AKT, EGFR, IRS-1, Shc, H-Ras, CDK1, G-protein alpha-s, G-protein beta/gamma, PI3K cat class 1A, c-Raf-1, p90Rsk, MEK2 (MAP2K2), PKA-cat, and PKA-reg.

8. The method of claim 1, wherein the platinum-based cancer treatment, taxane cancer treatment, gemcitabine, or oxazophorine treatment is cisplatin, carboplatin, paclitaxel, gemcitabine, or cyclophosphamide.

9. The method of claim 1, wherein the cancer is ovarian cancer, colon cancers, malignant glioma, breast cancer, leukemia, melanoma, non-small cell lung cancer, central nervous system cancer, renal cancer, or prostate cancer.

10. The method of claim 1, wherein high levels of BAD phosphorylation as compared to the median phosphorylation value indicate a poor prognosis for surgical cytoreduction survival.

11. A method of treating cancer in a patient in need thereof with platinum-based cancer treatment, taxane cancer treatment, gemcitabine, or oxazophorine treatment, comprising:
    determining clinical outcome or predicting clinical outcome of platinum-based cancer treatment, taxane cancer treatment, gemcitabine, or oxazophorine treatment comprising the steps of:
    obtaining a sample of a suspected or known cancer from the patient;
    measuring phosphorylation level of at least two BCL2 antagonist of cell death pathway proteins selected from the group consisting of MAP2K2, RAF1, HRAS, SHC1, EGFR, IRS1, PIK3CA, PIK3CB, PIK3CD, RPS6KA1, RPS6KA2, RPS6KA3, BAD, BCL2L1, BAX, AKT1, AKT2, AKT3, GNB1, GNB2, GNB3, GNB5, GNG10, LOC552891 GNG11, GNG12, GNG13, GNG3, GNG4, GNG5, GNG7, GNGT1, PPM1A, PPM1B, PPM1D, PPM1F, PPM1G, PPM2C, PTPN11, GNAS, PRKAR1A, PRKAR1B, PRKAR2A, PRKAR2B, CDC2, PRKACA, LOC730418, PRKACA, PRKACB, PRKACG, BAD phosphorylated serine 112, BAD phosphorylated serine 155, BAD phosphorylated serine 136, and a combination thereof;
    generating a BCL2 antagonist of cell death pathway signature score for the patient using average expression of the phosphorylation levels among the plurality of BAD pathway proteins using formula $\Sigma w_i x_i$, where $x_i$, represents gene i expression level and $w_i$, is the corresponding weight (loading coefficient) with $\Sigma w_2 i=1$;
    determining a median BCL2 antagonist of cell death pathway signature score using a highest value and a lowest value of the phosphorylation levels of the at least two BAD pathway proteins measured in the sample;
    determining the patient has a BCL2 antagonist of cell death pathway signature score above the median BCL2 antagonist of cell death pathway signature score by comparing the patient's BCL2 antagonist of cell death pathway signature score to the median BCL2 antagonist of cell death pathway signature score wherein a BCL2 antagonist of cell death pathway signature score above the median value in all analyses indicates positive clinical outcome to the treatment; and
    administering the platinum-based cancer treatment, taxane cancer treatment, gemcitabine, or oxazophorine treatment to the patient having the BCL2 antagonist of cell death pathway signature score above the median value.

12. The method of claim 11, wherein the phosphorylation level of a BCL2 antagonist of cell death pathway protein is detected using immunofluorescence.

13. The method of claim 11, wherein the platinum-based cancer treatment, taxane cancer treatment, gemcitabine, or oxazophorine treatment is cisplatin, carboplatin, paclitaxel, gemcitabine, or cyclophosphamide.

14. The method of claim 11, wherein the cancer is ovarian cancer, colon cancers, malignant glioma, breast cancer, leukemia, melanoma, non-small cell lung cancer, central nervous system cancer, renal cancer, or prostate cancer.

15. The method of claim 11, wherein BCL2 antagonist of cell death pathway signature score is evaluated using a log-rank test.

* * * * *

UNITED STATES PATENT AND TRADEMARK OFFICE
CERTIFICATE OF CORRECTION

PATENT NO.      : 9,528,982 B2
APPLICATION NO. : 14/010003
DATED           : December 27, 2016
INVENTOR(S)     : Johnathan Lancaster et al.

Page 1 of 1

It is certified that error appears in the above-identified patent and that said Letters Patent is hereby corrected as shown below:

In the Claims

Column 30, Claim 11, Line 49, should read:

corresponding weight (loading coefficient) with $\sum w_i^2 = 1$;

Signed and Sealed this
Seventh Day of March, 2017

Michelle K. Lee
*Director of the United States Patent and Trademark Office*